United States Patent [19]
Roizen et al.

[11] Patent Number: 5,341,291
[45] Date of Patent: Aug. 23, 1994

[54] PORTABLE MEDICAL INTERACTIVE TEST SELECTOR HAVING PLUG-IN REPLACEABLE MEMORY

[75] Inventors: Michael Roizen, Chicago; William E. Turcotte, II, Oak Park; Richard E. Pfisterer, Arlington Heights, all of Ill.

[73] Assignee: Arch Development Corporation, Chicago, Ill.

[21] Appl. No.: 27,920

[22] Filed: Mar. 8, 1993

Related U.S. Application Data

[60] Continuation of Ser. No. 794,295, Nov. 14, 1991, abandoned, which is a continuation of Ser. No. 497,891, Mar. 21, 1990, abandoned, which is a division of Ser. No. 130,934, Dec. 9, 1987, Pat. No. 5,025,374.

[51] Int. Cl.$^5$ .................... H03M 11/02; G06F 15/42
[52] U.S. Cl. .................... 364/413.02; 341/23
[58] Field of Search ............. 364/706, 413.01, 413.02, 364/709; 341/22-23

[56] References Cited

U.S. PATENT DOCUMENTS

| | | | |
|---|---|---|---|
| 3,566,370 | 2/1971 | Worthington | 364/900 |
| 3,839,708 | 10/1974 | Bredesen et al. | 340/172.8 |
| 3,934,226 | 1/1976 | Stone et al. | 364/200 |
| 4,130,881 | 12/1978 | Haessler et al. | 364/413.02 |
| 4,365,315 | 12/1982 | Jamnik | 364/419 |
| 4,464,122 | 8/1984 | Fuller et al. | 364/413.01 |
| 4,545,023 | 10/1985 | Mizzi | |
| 4,680,731 | 7/1987 | Izumi et al. | 364/900 |

FOREIGN PATENT DOCUMENTS 1217344  3/1986  U.S.S.R. .................... A61B 5/16

OTHER PUBLICATIONS

"A Decision-Driven System to Collect the Patient History", Hang et al. Computers and Biomedical Research 20, 193-197, 1987.
"Historymaker", Medical Logic International; Sep. 1983, Microsearch File (Orbit), AN 83-007531.
"First Opinion", Medical Logic International, Sep. 1983, Microsearch File Orbit, AN 83-007528.
*Comp. Info Processing & Telecommunications;* second edition Jerry M. Rosenberg, 1984.
Skier, Ian "The Hewlett-Packard HP-75", Popular Computing vol. 2 No. 4 98/3P, Feb. 1983, Abst. from Microsearch file Orbit AN 83-006335.

*Primary Examiner*—Gail O. Hayes
*Attorney, Agent, or Firm*—Laff, Whitesel, Conte & Saret

[57] ABSTRACT

An interactive medical test selector for use by a patient is about the size of a book and has a screen for displaying questions to a patient, a limited number of keys by which the patient can enter answers, and a memory device for storing the patient's answers. The test selector is battery-powered for portability and uses a low-power liquid crystal display or the like to display instructions and medical questions to the patient. Only four keys are seen or used by the patient for answering the questions: YES, NO, NOT SURE, and NEXT QUESTION. Additional control keys used by the medical staff are hidden from the patient. The device is controlled by a pre-programmed microcomputer on a chip, and a ROM-based, removeable and replaceable control program which not only collects, but also analyzes the patient's answers and makes appropriate recommendations based on those answers, and drives a remote printer or computer terminal.

22 Claims, 20 Drawing Sheets

HAVE YOU TAKEN ASPRIN, EXCEDRIN, ANACIN,
BUFFERIN, ALKASELTZER OR ANY SIMILAR
MEDICATIONS IN THE LAST WEEK?
                                    NOT SURE

— 22

YES | NO | N.S. | NEXT QUES.

ANSWER BUTTONS

THIS COMPLETES THE QUESTIONNAIRE.
THANK YOU FOR YOUR TIME.
PLEASE RETURN THIS UNIT FOR ANALYSIS.

— 22

YES | NO | N.S. | NEXT QUES.

ANSWER BUTTONS

QUESTIONAIRE COMPLETED
ENTER ACCESS CODE
XXXX

— 22

| 1 | 2 | 3 |
| 4 | 5 | 6 |
| 7 | 8 | 9 |
| * | 0 | # |

YES | NO | N.S. | NEXT QUES.

ANSWER BUTTONS

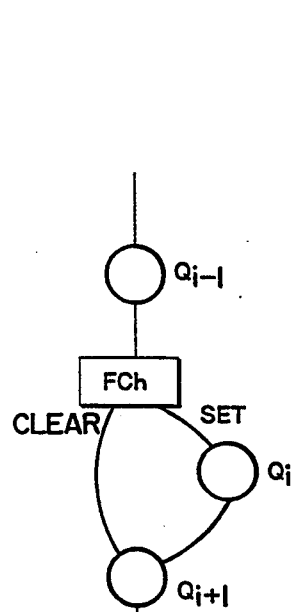
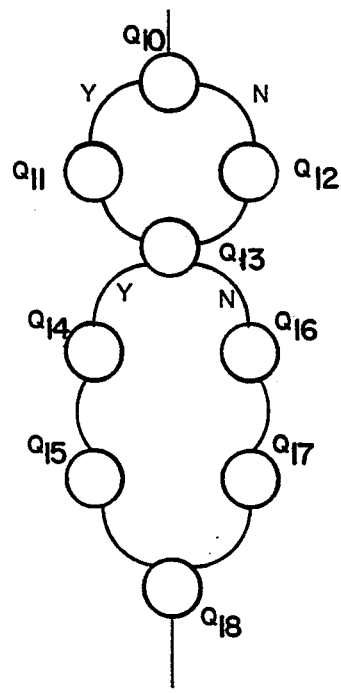
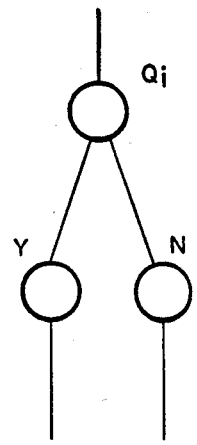
FIG. 13A　　FIG. 13B　　FIG. 13C　　FIG. 13D
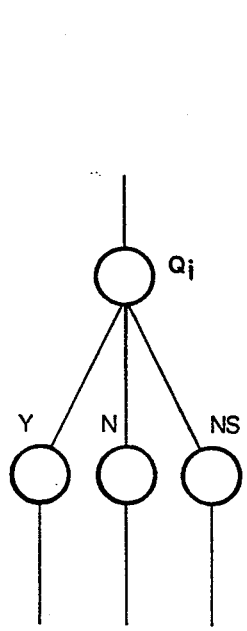
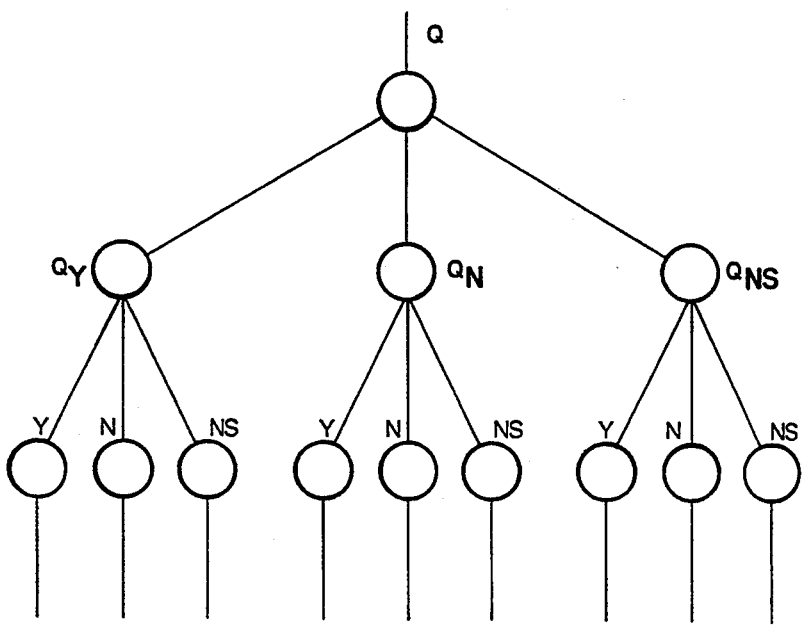
FIG. 13E　　　　　　　FIG. 13F

PORTABLE MEDICAL INTERACTIVE TEST SELECTOR HAVING PLUG-IN REPLACEABLE MEMORY

This application is a continuation of application Ser. No. 07/794,295, now abandoned filed Nov. 14, 1991, which is a continuation of application Ser. No. 07/497,891, now abandoned filed Mar. 21, 1990, which is a division application Ser No. 07/130,934, filed Dec. 9, 1987, now U.S. Pat. NO. 5,025,374.

NOTICE REGARDING COPYRIGHTS

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

This invention relates to a medical test selecting device, and more particularly to a portable computerized device which administers a questionnaire to a patient, especially a surgical patient, even if the patient is bedridden, and is capable of printing out a full report including advice to a physician as to what pre-operative or other medical tests are indicated for that patient.

BACKGROUND OF THE INVENTION

It has been estimated that of the approximately $30 billion spent each year in the United States for medical tests, as much as 60% of that amount ($18 billion) is wasted on unnecessary tests; i.e., those which, for a given patient, would not be needed if the physician had the benefit of a reliable medical history. See, for example, *Are We Hooked on Tests*, U.S. News & World Report, Nov. 23, 1987, pp. 60–65, 68–70, 72.

This problem of unnecessary testing is particularly acute in cases where a patient is about to undergo surgery and, in order to determine the proper anesthesia, the patient's general medical history is taken.

This medical history strongly influences which diagnostic tests the medical staff chooses to perform before surgery. For example, if the patient discloses that he or she has any pain or discomfort upon urination, or has noticed any blood in the urine, then a urinalysis (a chemical analysis of the urine) ought to be performed. But if those symptoms are not present, it is considered medically unnecessary to administer a urinalysis, absent some other medical indication for the test.

Under current medical practice, it requires about seventy-five or more questions to determine which, if any, of the various available pre-operative tests (urinalysis, chest x-rays, EKG, etc.) might have to be performed before determining what anesthesia ought to be used during surgery. If the physician is not sure that all these questions were properly asked, or has doubts about the care with which the patient's answers have been recorded, he or she is likely to include in the battery of preoperative tests many that could have been excluded based on an accurate patient history.

To save the time of physicians, questionnaires have been devised that can be administered by a nurse or other trained medical worker, or even directly filled in by the patient. But the time of a trained medical worker is also too valuable to spend on such tasks, since that makes the individual unavailable to perform other, more pressing, medical tasks which require such training.

If the patient completes the questionnaire alone, he or she may overlook or ignore some of the questions. Also, if the patient usually reads in a foreign language or has vision problems, he or she may have trouble completing the questionnaire alone.

Even if a questionnaire is fully and properly filled out, tallying of the patient's answers to determine which tests are needed is a time-consuming and tedious task, in the course of which medical workers sometimes inadvertently introduce errors.

Because of these problems, all too often a reliable medical history of this type is not taken prior to surgery, in which case the patient may have to undergo a comprehensive battery of preoperative tests, many of them unneeded. These unnecessary tests are expensive for the patient and a burden on an already overworked medical system. In addition, the more tests are done the greater is the risk of false positives and iatrogenic harm from pursuit of false positives. Therefore, there is a great need to "automate" the reliable taking and tabulating of preoperative test questionnaires.

THE PRIOR ART

The prior art has proposed the use of computers or computer terminals to automate the taking of general-purpose medical histories. For example, in U.S. Pat. No. 3,566,370 of Worthington et al. a computer terminal which is connected by telephone lines to a mainframe computer displays questions on a CRT screen which are to be answered by the patient sitting at a full alphanumeric keyboard. After the patient answers the questions, the computer stores, formats and prints out the patient's medical history. The Worthington patent also suggests that the questions presented to the patient for the purpose of taking his medical history can be in foreign languages when necessary. U.S. Pat. No. 4,130,881 of Haessler et al. is similar to Worthington in many respects.

Published Japanese Patent Application No. 59-231676 is similar to the above-mentioned U.S. patents in its use of a computer console and full alphanumeric keyboard, except that in addition the computer there is programmed to develop recommendations. The recommendations are intended for the guidance of Japanese pharmacists, not medically trained physicians, in prescribing oral medications according to Chinese traditional folk medicine criteria. To date no computerized system has been developed which is specifically programmed to administer the particular sequence of questions which is considered appropriate for pre-operative test selection according to accepted western scientific medical criteria.

General-purpose computing machines of the type employed in the above prior art patents are much too expensive, bulky, and complicated for the task of automating the pre-operative test selection process. Moreover, the great majority of patients are not "computer literate" and find such equipment difficult to use even when they are feeling well. A patient who is about to go into surgery in the very near future is particularly likely to find a large-scale general-purpose computer system confusing and threatening. The problem is exacerbated by the fact that these computers require the patient to compose an answer on a keyboard containing the full range of alphanumeric characters and other keys.

The prior art has recognized the need in certain contexts for a simplified special-purpose data-processing device which offers the non-computer-literate person a simple choice between "yes" and "no" answers, as in published French Patent Application No. 77 17048. But the computer in that application is programmed to recommend a skin cosmetic regime rather than a medical treatment procedure.

A pre-operative patient is sometimes in such poor condition that it would be physically difficult to get out of bed and sit at the keyboard of large-scale computer system. Ideally, therefore, an automated pre-operative test recommendation device would be small enough to be portable. Here again, the prior art does have examples of portable special-purpose computers, but these too have not been adapted for use in a pre-operative test selection environment. The portable computer in U.S. Pat. No. 4,686,624 of Blum et al., for example, is dedicated to controlling the dietary habits of diabetics.

BRIEF SUMMARY OF THE INVENTION

Accordingly, one general object of the invention is to provide an automatic device for taking patient histories which is especially adapted for the selection of medical and/or preoperative tests, and can be easily used even by bed-ridden patients. A more particular object is to provide a small, battery-powered, portable dedicated computer that automatically displays questions and enables a non-computer-literate patient to answer by means of only a few keys. A further object is to provide such a device that automatically analyzes the patient's answers to determine which tests appear to be necessary, and provides a printed report. Yet another object is to provide a device which is medically reliable, but is nevertheless relatively inexpensive. It is also desirable to provide a device of this type which can be easily be field-modified to update the questions at intervals to keep up with the progress of medical knowledge. Such a device should also be capable of communicating with either the patient or the doctor in a foreign language when necessary.

The invention provides a hand-held, battery-powered medical and/or pre-operative test selector for use by a patient which has means for displaying questions to a patient, a limited number of keys by which the patient can enter answers, and a memory device for storing the patient's answers. Alternatively, an audio jack enables the patient to listen to the questions with earphones. The device preferably uses a low-power display such as a liquid crystal or the like. In a preferred embodiment, no more than four keys are used by the patient: YES, NO, NOT SURE, and GO TO NEXT QUESTION (hereafter "NEXT QUESTION"). Additional control keys may be provided for use by the medical staff, but are hidden from the patient. The device is controlled by a pre-programmed microcomputer on a chip which stores in a memory the text of user instructions, medical or pre-operative questions, and words to be used in printed reports. The microcomputer is programmed to tally the patient's answers and, on the basis of that information, to indicate which tests are advisable. The test selector can be provided with additional prestored text so the user has the option of displaying questions in more than one language, or being asked the questions in an audio mode. The questions and the software for recommending pre-operative tests are stored in a readily removable and replaceable integrated circuit chip to facilitate updating of the questions and/or the test selection procedure at intervals, as medical knowledge advances.

BRIEF DESCRIPTION OF THE DRAWINGS

These mentioned and other features of the invention will become more apparent, and the operation of the invention will be best understood, by reference to the following detailed description of preferred embodiments of the invention, when taken in conjunction with the accompanying drawings, in which:

FIGS. 3A–3F are views of the display and control keys of the test selector when it is in various modes of operation;

FIGS. 13A–13F show nodes representing questions to be asked and various arrangements of program paths linking the questions.

DETAILED DESCRIPTION OF THE PREFERRED EMBODIMENT

1. GENERAL APPEARANCE AND FUNCTIONS

Figure 1:
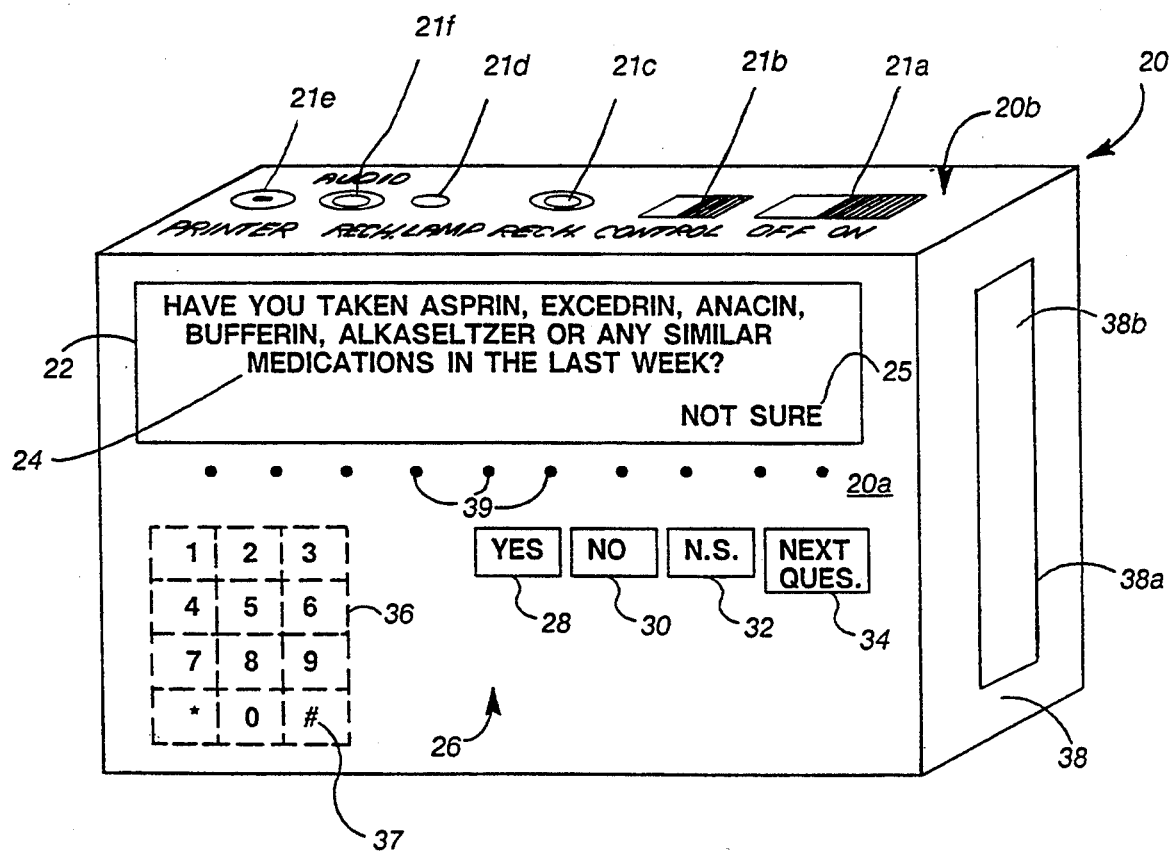
FIG. 1 is perspective view of an exemplary pre-operative test selector according to the invention.

A portable interactive test selector 20 embodying the invention is shown in FIG. 1, in the Question & Answer (Q&A) mode used by a patient. Preferably it is battery-powered and about the size of a book or calculator so that a patient can operate it on his or her lap, or at a desk or table. Built in to an operating panel 20a are a text display 22 and a patient keypad 26.

The operating panel also has a control keypad 36 which is kept inconspicuous or hidden from the patient. For example, the control keypad may be concealed by a translucent plastic sheet, but have labeled keys that can be illuminated to make the key labels visible from behind the translucent sheet. Or the control keypad can be hidden from the patient behind a sliding panel or the like.

Yet another alternative for the control keypad 36 is to provide a row of small, unlabeled, switch buttons 39 just below text display 22. When these switches 39, which can be membrane switches or nonmoving capacitance-sensitive switches, are activated by a medical staffer, numerical labels for them (not shown) can be made to appear in the bottom row of display 22.

Test selector 20 also has a back panel 20b, on which are arrayed an ON/OFF switch 21a, a control button 21b, a socket 21c for a battery recharger, a recharging lamp 21d, a printer jack 21e, and an audio output jack.

A side panel 38 of the test selector has a recess 38a for receiving a read-only memory (ROM) cartridge 38b for updating a control program and test information.

A series of prestored YES/NO questions 24 for the patient appear one at a time on text display 22, to each of which the patient responds in turn by pressing an appropriate answer key on the patient keypad 26. Alternatively, the coded sounds for these questions can be stored in a speech ROM and converted from digital to analog to give an audio reading of the questions to the patient via a speaker or headphones using audio jack 21f.

Keypad 26 has only a very limited number of keys, such as four keys 28-34 for the choices YES, NO, NOT SURE (N.S.), and NEXT QUESTION. Pressing an answer key 28, 30, 32 causes the answer chosen to be echoed in the display as input echo 25. For example, in FIG. 1, the patient has pressed the NOT SURE key, causing the text "NOT SURE" to appear in the display as input echo 25.

However, the answer echoed on the display at 25 is not considered the patient's final answer until the patient presses a NEXT QUESTION key 34, which acts like the "Enter" or "Return Key" on a microcomputer. Until Next Answer key 34 is pressed, the patient can change the echoed answer by pressing one of the other answer keys, then press the "NEXT QUESTION" key to adopt it as his or her final answer.

As will be seen below, a patient is instructed that if he or she has answered a question by pressing one of answer keys 28, 30, 32 and "NEXT QUESTION" key 34 and afterwards wants to go back to that question, the test selector should be returned to the medical staff for resetting. Then a staff person uses control key 21b to illuminate control keypad 36, and presses backup key 37 to back up the display to the prior question. This enables the patient to enter a revised answer by one of keys 28, 30, and 32, followed by NEXT QUESTION key 34.

It has been found that this very limited set of keys makes it easy for even the typical non-computer-literate patient to use the test selector with little or no instruction. To the typical patient, these keys are as easy as, or easier than, as those found in elevator controls, simple household appliances, etc.

Figure 2:
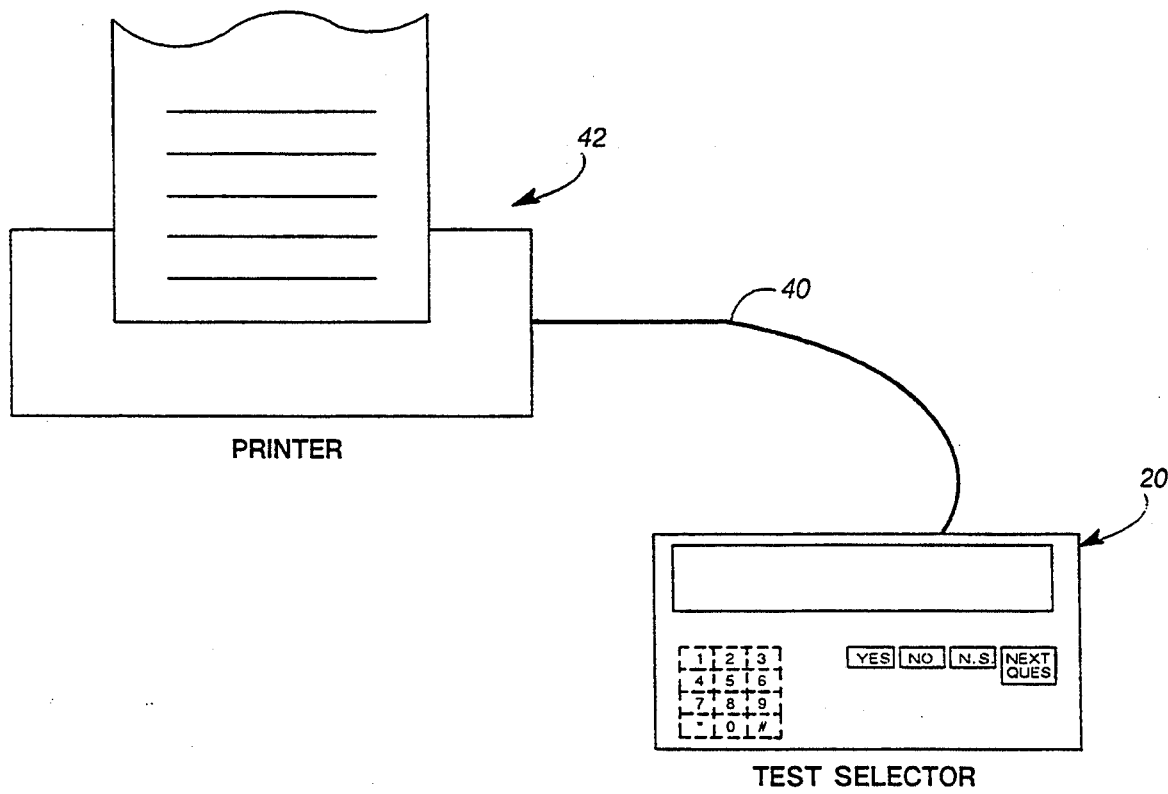
FIG. 2 is a diagram showing the test selector connected to a printer to produce printed output.

As shown in FIG. 2, when the patient has read and answered a full set of questions, test selector 20 can be attached by a printer cable 40 to a standard ASCII printer 42 to print out reports based on the patient's answers. A plug (not shown) on printer cable 40 is inserted into printer jack 21e.

Preferably, the printer has an input for serial data complying with the popular interface standard RS-232C of the Electronic Industry Association, and the handshaking between the test selector and printer is software controlled. Then cable 40 will only need three lines: a line for data and control signals transmitted by the test selector and received by the printer, a line for data and control signals transmitted by the printer and received by the test selector, and a ground or common connection.

In such a case, printer jack 21e and its matching plug (not shown) can be simple miniature three wire stereo jacks, such as are found on audio equipment for connecting stereo headphones. Such jack and plug sets are compact, lightweight, and snap together and apart easily, making them much easier to use than standard 25 or 9 pin serial connectors for microcomputer equipment.

2. GENERAL METHOD OF OPERATION

Figure 3A:
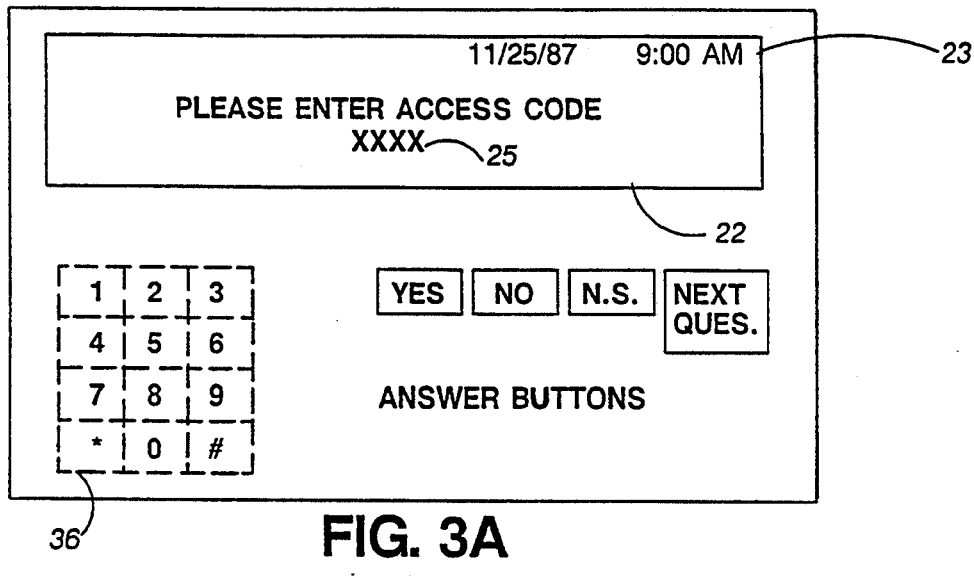

In operation, the medical staff person administering the test (hereafter "staffer") controls the mode of the test selector by selecting from choices presented by display 22, as shown in FIGS. 3A–3F. When the test selector is first turned on, control keypad 36 is lit or otherwise made usable as shown in FIG. 3A, and display 22 prompts "PLEASE ENTER ACCESS CODE". In response, the staffer must enter a four digit secret access code (password) via control keypad 36. The four integers keyed in by the staffer are echoed on display 22 merely as X's to keep the access code secret.

Figure 3B:
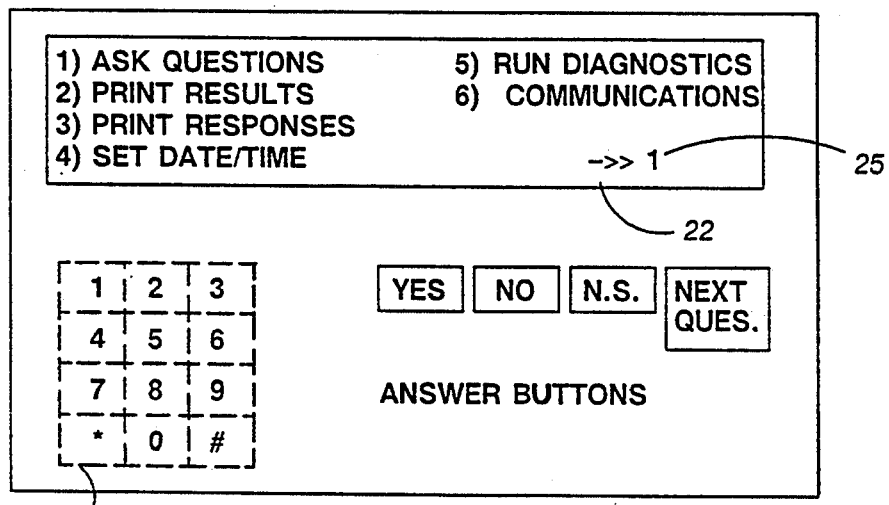

If the staffer's access code is correct, FIG. 3B, the display changes to an opening menu offering the following choices:

1) ASK QUESTIONS
2) PRINT RESULTS
3) PRINT RESPONSES
4) SET DATE/TIME
5) RUN DIAGNOSTICS
6) COMMUNICATIONS

The control keypad remains lit or otherwise usable for the staffer's choice, which appears as input echo 25.

Figure 3C:
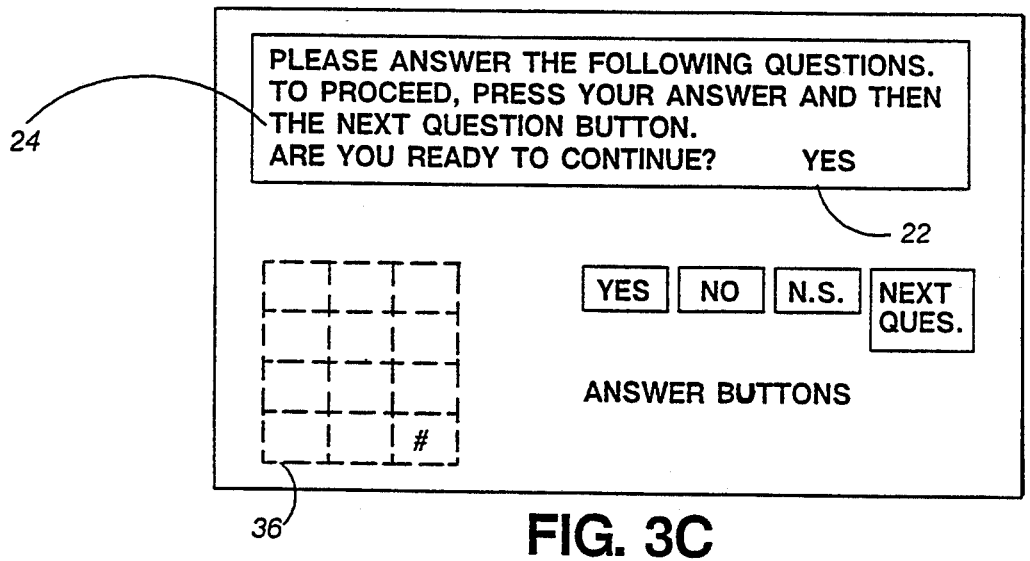

Suppose, as in FIG. 3B, that the staffer presses 1 on the control keypad for the selector to administer a questionnaire to a patient. Then as shown in FIG. 3C, the illumination of the control keypad is turned off, concealing it, and the display shows an introductory message and an initial prompt for the patient to confirm that he or she has read the message:

PLEASE ANSWER THE FOLLOWING QUESTIONS. TO PROCEED, PRESS YOUR ANSWER AND THEN THE NEXT QUESTION BUTTON. ARE YOU READY TO CONTINUE?

Then the display shows a brief series of introductory screens about the way the patient should operate the test selector. This introduction advances by one screen each time the patient presses an answer key followed by the NEXT QUESTION key to indicate that he or she is ready for the next instruction.

With the introductory screens completed, the first medical history question appears in display 22, as shown in FIG. 3D.

When the patient has read and responded to each of the prestored questions, a message appears in display 22 asking that the test selector be returned to the staffer for analysis. The next time any key is pressed, the test selector illuminates the control keys and displays a prompt for the staffer to enter his or her access code. If the staffer's access code is accepted, a command menu similar to that of FIG. 3B appears from which the staffer can choose the next mode of operation.

Usually the staffer's choice will be to press control key 2 to print a report for the patient's physician (see Appendix I) or control key 3 to print a "hard copy" of the patient's questions and answers for signature by the patient (see Appendix II). The printed copy for signature can include various notices and disclosures to the patient, and follow-up questions with blanks where the patient can fill in a response. For example, if the patient has answered "YES", he or she has allergies, a follow-up question will be printed at the top of the hard copy for completion:

WHAT ARE YOU ALLERGIC TO?___

3. CONNECTION TO WORK STATION

Figure 4:
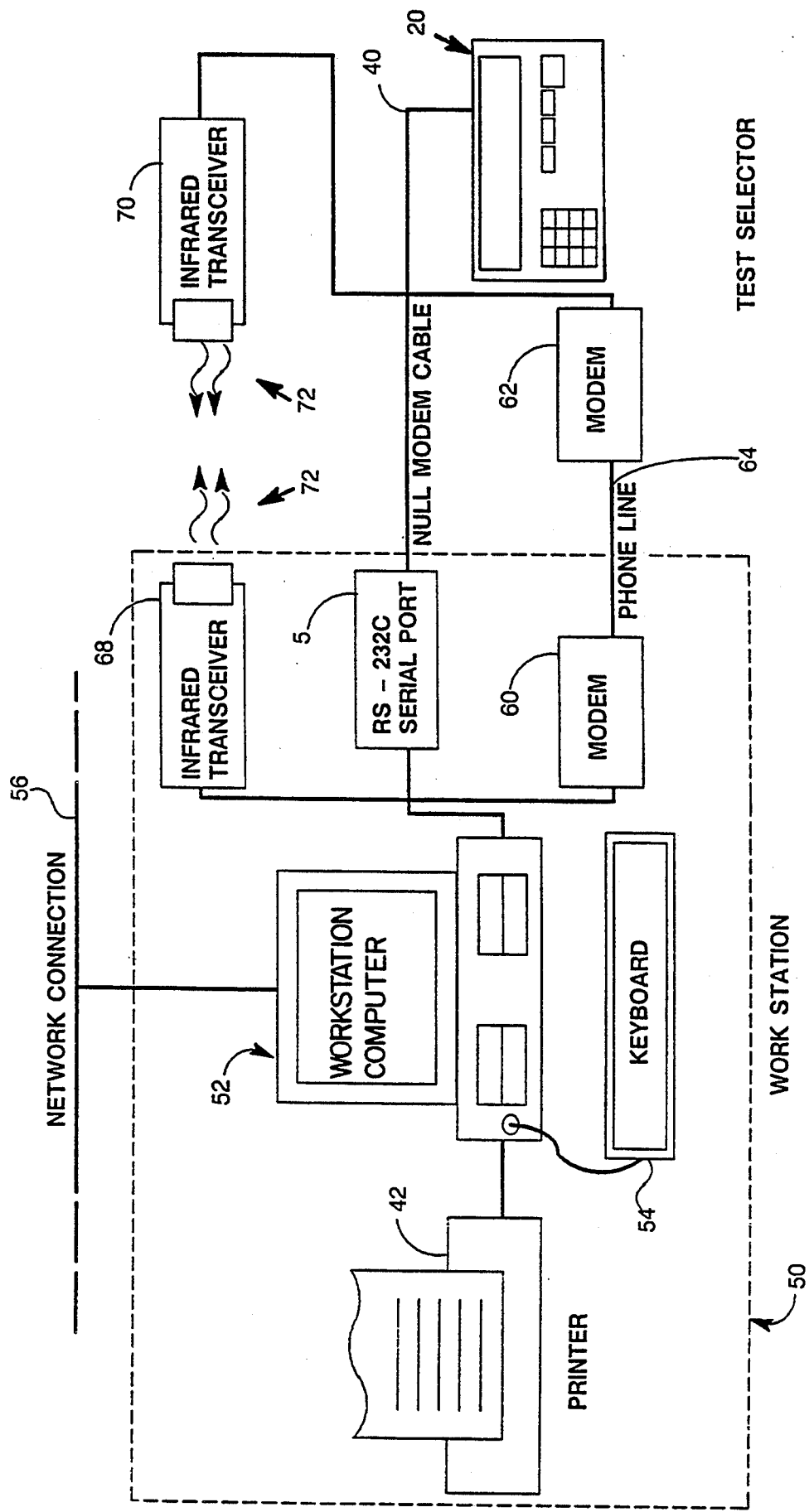
FIG. 4 is a diagram showing the test selector coupled to a computer terminal.

In addition to being printed out, the machine-readable reports and the patient's responses can be transmitted as shown in FIG. 4 to whatever computerized medical record-keeping or management system is being used by the patient's physician or hospital. For example, the physician or hospital may use a computerized workstation 50 having a microcomputer or terminal 52 with keyboard 54, a printer 42, and an RS-232C serial port 57 for data communications. The microcomputer or terminal 52 may be coupled to a larger system, such as a hospital or laboratory mainframe computer, by a network connection 56.

Test selector 20 can be directly coupled by a serial cable 40 to an RS-232C interface of the workstation for uploading of the question and answer data obtained from the patient, or downloading of data such as the patient's name, as entered on keyboard 54 of the workstation's computer 52, for use in the reports printed under direction of test selector 20.

If the test selector is being used in a location remote from the work station, each can be coupled for communication to a common phone line (external or intercom) by respective modems. In a preferred embodiment of the invention, to eliminate the need for actual mechanical coupling of electrical connectors, the workstation is provided with an infrared transceiver 68 which uses infrared signals 72 to transfer data to and from a similar infrared transceiver 70 that is coupled to test selector 20.

4. CIRCUIT CONSTRUCTION

Figure 5:
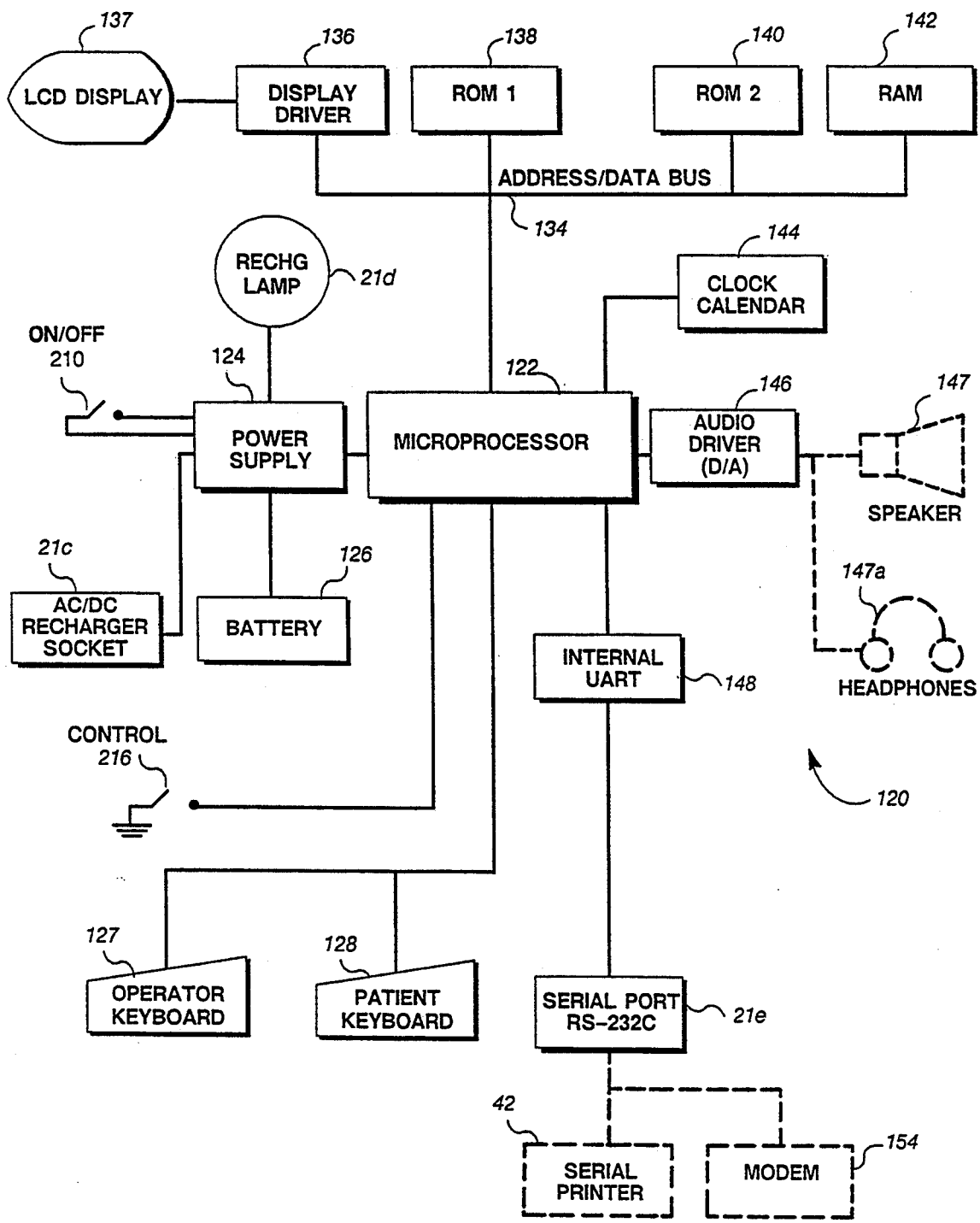
FIG. 5 is a functional block diagram of the main hardware components used in the test selector, and their interconnection.

The test selector of the present invention can be conveniently and inexpensively realized by means of the microprocessor-based circuit 120 shown in the functional block diagram of FIG. 5. A microprocessor 122 receives its operating voltage from a power supply 124 that regulates the power from a rechargeable battery 126. The power supply is controlled by the ON/OFF switch 21a of FIG. 1, and can receive external electrical power for recharging battery 126 via AC/DC recharger socket 21c. Charging lamp 21d is lit whenever power supply 124 is recharging battery 126 from the external power. When battery 126 is fully charged, the charging automatically stops and charging lamp 21d goes out.

An operator keyboard 127 and a patient keyboard 128 are each coupled to ports on the microprocessor to provide digital input data from the medical staff and patients. Control switch 21b is connected to an input terminal of the microprocessor. When the patient is answering questions, the operator keyboard 127 is not illuminated to conceal it. However, if a staffer presses control switch 21b, microcomputer 122 relights control keypad 127 so the staffer can use backup key 37 of FIG. 1 to return the display to a previous question for the patient.

The microprocessor has a multiplexed address and data bus 134 by which it is able to send data bytes to a display driver 136, read-only memories ROM 1 and ROM 2, and a scratchpad random access memory RAM 142. Display driver 136 delivers ASCII text data to a display 137, which, for example, can be a supertwist liquid crystal display (LCD) capable of displaying four lines of forty characters. Preferably the character set includes not only the usual 128 ASCII characters, but an additional 128 symbols which include the international letters and symbols needed for foreign alphabets.

ROM 138 serves as a primary read-only memory in which can be stored the operating program for the microcomputer and the text used for the test selector's questions, answers, and reports. ROM 140 is optional, and when present serves as a secondary read-only memory which stores an alternate language version of the text data for the test selector's questions, answers, and reports. Thus, ROM 2 makes it possible for the questions, answers, and/or reports to be displayed by display 137 and/or printed out in a second language.

It is an important feature of the invention that ROMS 1 and 2 can be easily replaced by an untrained medical staffer. For example, they can be combined in ROM cartridge 38b for easy removal and insertion into recess 38a of side 38 of the test selector. This enables the control program, the questions asked, and the recommendations to the doctor to be easily updated to the latest version.

Suppose ROM 1 holds English text because the physician's office primarily uses English, but the patient primarily reads Spanish. If ROM 2 stores a Spanish version of the text of the questions, answers, and reports, by a software selection portions of ROM 2 can be addressed in place of those in ROM 1 to display the questions and answers in Spanish. The questions and answers, and follow-up questions can also be printed in Spanish. However, the staff can revert back to ROM 1 for an English version of the questions and answers and an English report of results to the physician.

A clock/calendar chip 144 is provided so that the time and date 23 can appear in the display (FIG. 3A) and be stamped on the printed reports and questionnaires. Moreover, since medical information and practice are constantly being updated, if desired the time and date information can be used to automatically check an expiration or date stored with the medical data in ROM 1. If the data in ROM 1 becomes older than this date, a notice can be included in the display or in the printouts, or the test selector can be prevented from functioning until the ROM is updated.

If desired, an audio driver 146 can be coupled to an output port of microprocessor 122, to enable the microprocessor to send tones, sounds, or voice information to users via an external speaker 147 or headphones 147a via the audio jack 21f of FIG. 1.

To convert the microprocessor's parallel data into serial signals, microprocessor 122 includes an internal universal asynchronous receiver/transmitter (UART) 148 which is coupled to an output RS-232C-compatible serial connector 21e. To print reports, a standard serial printer 42 can be attached to connector 21e.

In the embodiment of the example, microprocessor 122 can be an eight-bit Hitachi Ltd. HD6303 chip of low power CMOS construction. Mode 3 of this single chip processor configures it to run as a microprocessor with a sixteen-bit (64K) address bus and an eight-bit data bus. An external crystal is used to maintain a clock frequency of about 4 MHz. The relatively large 64 kilobyte (KB) external address space easily enables external RAM 142 to be a two-KB scratchpad memory, and the external ROM 138 to be provided with about 8 KB of program code and 24 KB of text and related data for the questions, answers, and reports. Moreover, there is still plenty of room for second language ROM 140.

The program for this microprocessor, was written in Microtext Assembler language, which is compatible with the assembler language produced by Motorola. A source code listing for a first embodiment is attached to this application as Appendix III, and a source code listing for a second embodiment of the invention is attached as Appendix IV.

5. SOFTWARE CONSTRUCTION a. Generally

Figure 6:
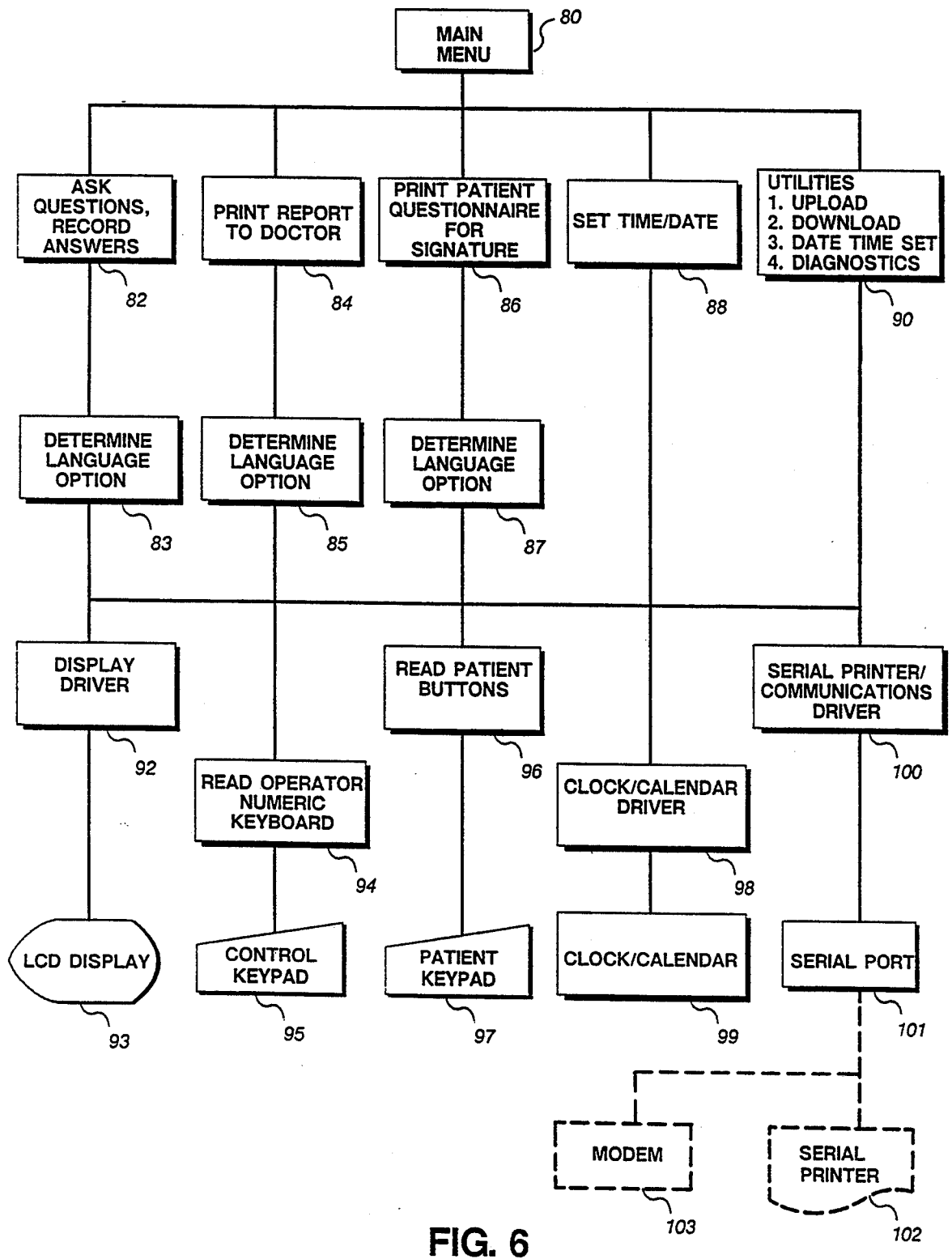
FIG. 6 is a diagrammatic representation of a program used to control the test selector, showing a functional representation of the systems software.

The various operations carried out by the microprocessor-based circuit of FIG. 5 are represented in the functional block diagram of FIG. 6. The main operating routine displays the Main Menu 80 (see FIG. 3B), prompting the medical staff to choose one of the main subroutines by entering a menu number via the control keypad.

The main subroutines are those for Asking Questions and Recording Answers 82, Printing a Report for the Doctor, Printing the Patient's Questions and Answers for Signature, Setting the Time and Date 88, and various Utilities 90. If optional language ROM 2 is installed, whenever 82, 84, or 86 is selected, the language that should be used is next determined by a corresponding language option routine 83, 85 or 87.

An important feature of the invention is that reports and questionnaires can be automatically date stamped, and the medical information in ROM 1 can be automatically checked to see if it should be renewed. However, this requires that subroutine 88 be provided to enable the clock/calendar chip 144 to be properly set by the medical staff or at the factory prior to shipping.

Subroutine 90 includes various utilities, such as dedicated communication programs for uploading or downloading data to workstation 50 of FIG. 4 or running diagnostics to check circuit and data integrity.

Supporting the above-mentioned high-level subroutines are various lower-level input/output routines that interface with the hardware. Display driver 92 manages the data flow to LCD display 93. The subroutines 94 and 96 respectively get staffer and patient input from the control and patient keypads. Clock/calendar driver 98 makes clock/calendar 99 software accessible, and drivers 100 for the serial printer 102 and serial communications control input/output to serial port 101 or an external modem 103.

b. Main Menu Routine

Figure 7:
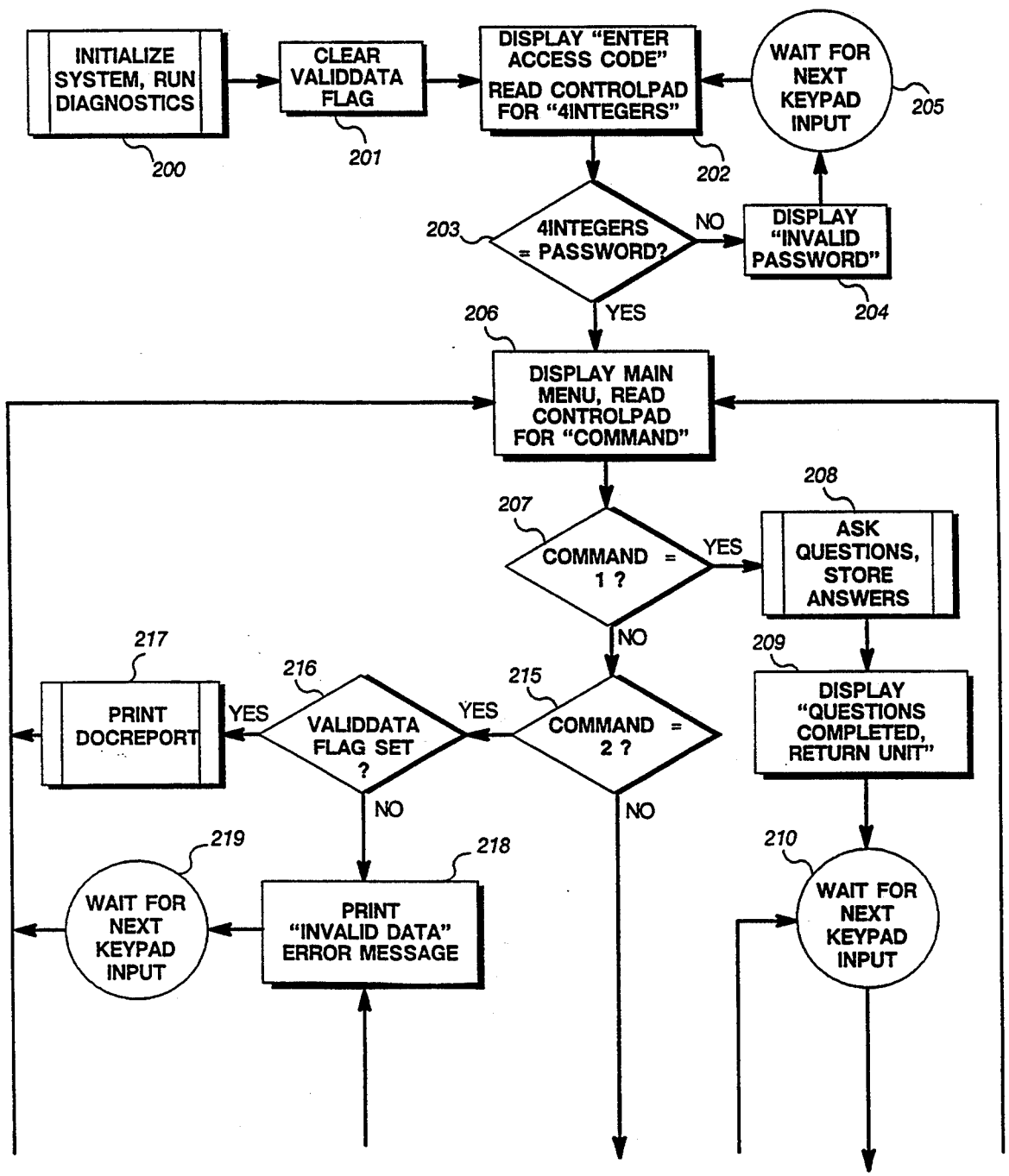
FIG. 7 is a flowchart of the Main Menu program shown in FIG. 6.
Figure 7:
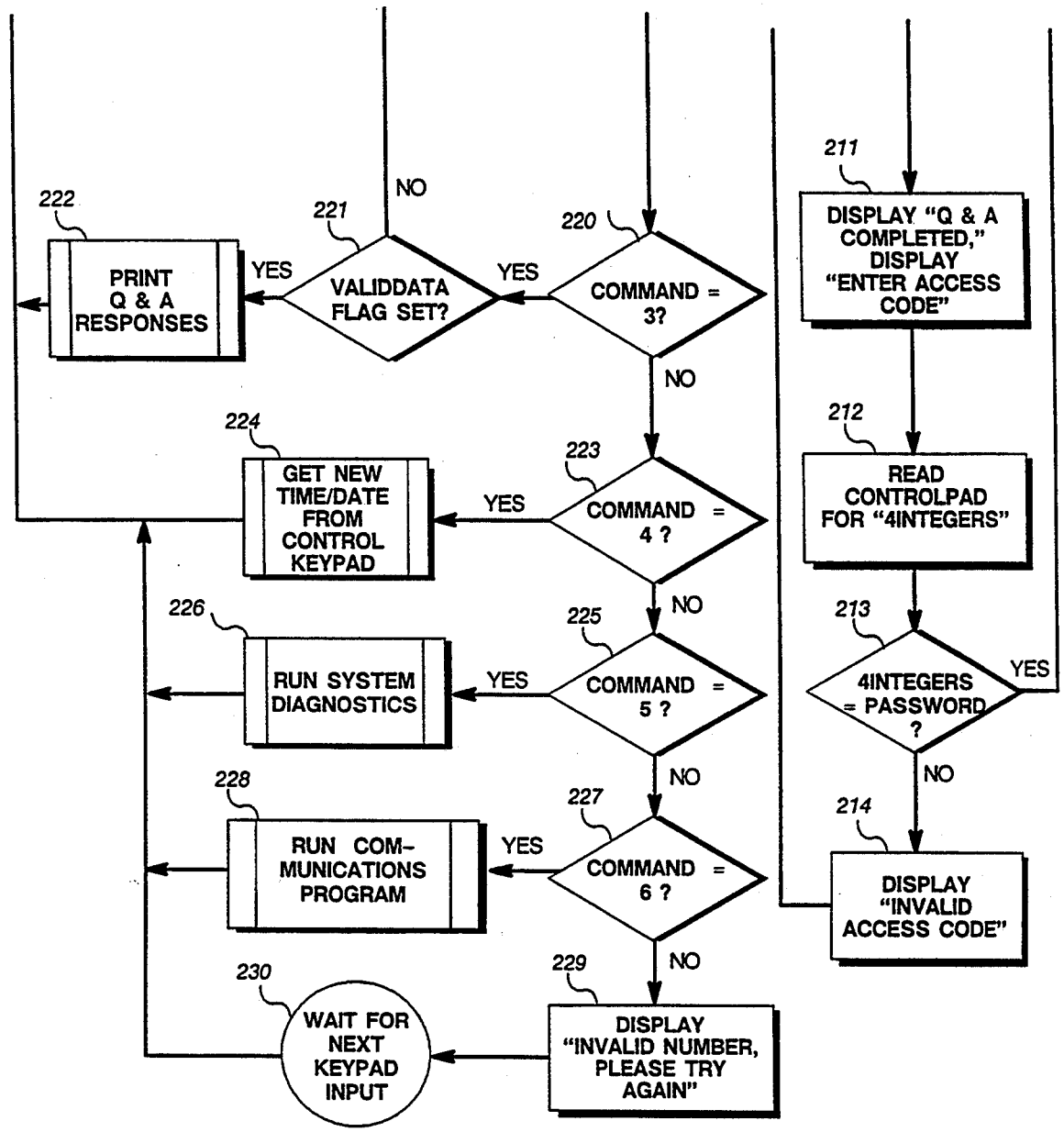

As shown in FIG. 7, Main Menu routine is the first routine called when power is provided to the microprocessor system. At Step 200 the system is initialized and diagnostics run, after which at Step 201 a flag called VALIDDATA is cleared. The message "ENTER ACCESS CODE" shown on display 22 by STEP 202, and the control pad read for the secret four-integer access code entered by the medical staffer. If Step 203 determines that the four integers read are not a valid access code, Step 204 puts "INVALID PASSWORD" on display 22, and at Step 205 this error message is left in place until there a further input is read from the control keypad at Step 202.

When Step 203 finds that a valid access code has been input, at Step 206 the Main Menu of FIG. 3B is displayed, and the medical staffer asked to enter a command integer 1-6. If the command integer is 1, Step 207 calls a subroutine ASK QUESTIONS, STORE ANSWERS at Step 208. This subroutine administers the prestored medical questionnaire to the patient and stores his or her answers. As subroutine 208 is completed, it sets the VALIDDATA flag (step not shown). Next at Step 209 "QUESTIONS COMPLETED, RETURN UNIT" is displayed to the patient. Step 210 keeps this message on the display until the next keyboard input.

When the patient returns the test selector to the medical staffer, and a key of the control pad is touched, the wait at Step 210 ends and "Q&A COMPLETED, ENTER ACCESS CODE" is displayed to the medical staffer. When Step 213 find that the staffer again enters a valid four-integer access code, a jump is made at Step 214 back to the main menu display of Step 206. But if the code is wrong, a jump is made back to Step 210 to request the access code again.

Suppose that a set of valid question and answer data has been taken, a proper access code entered by the medical staffer at Step 212, and a jump made back to the Main Menu of Step 206. The medical staffer will probably now select a printout option, either command integer 2 (prints a report for the doctor) or 3 (prints the questionnaire with follow-up questions, etc.). If command integer 2 is selected, Step 207 will be a "NO" and Step 215 will be a "YES". Step 216 then checks to see if the VALIDDATA flag is set to avoid printing partial, meaningless, or corrupted data. If VALIDDATA flag is set, at Step 217 a subroutine PRINT DOCREPORT prints a report with test recommendations for the doctor. An example of such a report appears as Appendix I.

If at Step 216 the VALIDDATA flag is found not to be sent, a jump is made to Step 218, which prints an error message "INVALID DATA", after which Step 219 waits for the next keypad input and then causes a jump back to the Main Menu 206.

When the command integer selected by the staffer at Step 206 is a 3, Steps 207 and 215 both "NO" and Step 220 is "YES". This causes Step 221 to check if the VALIDDATA is set: if it is, the PRINT Q&A RESPONSES subroutine of Step 222 prints the questions and the patient's answers, and then jumps back to the main menu. But if Step 221 finds that the VALIDDATA flag is not set, a jump is made to print the error message of Step 218, pause until the next key input at step 219, and jump back to the main menu of Step 206.

Of course, the staffer may select a housekeeping function at Step 206, such as command integer 4, which passes as a "NO" through steps 207, 215, and 220, but is a "YES" for Step 223. This causes the subroutine of Step 224 to get a new time or date from the control keypad, i.e., let the medical staffer set the clock/calendar.

Or the staffer may select command integer 6, which at Step 227 causes a communications subroutine 228 to run so that data or patient information, such as medications, birthdate, or responses to questions, can be transferred to or from the test selector to a work station or the like.

If the command integer is other than 1-6, the program will pass to Step 229, which puts "INVALID NUMBER, PLEASE TRY AGAIN" on the display. After a wait at Step for 230 for keypad input, the routine jumps back to the Main Menu. Note that, barring a crash of a subroutine, the Main Menu routine runs in an endless loop.

c. Accommodating A Second Language

Figure 8A:
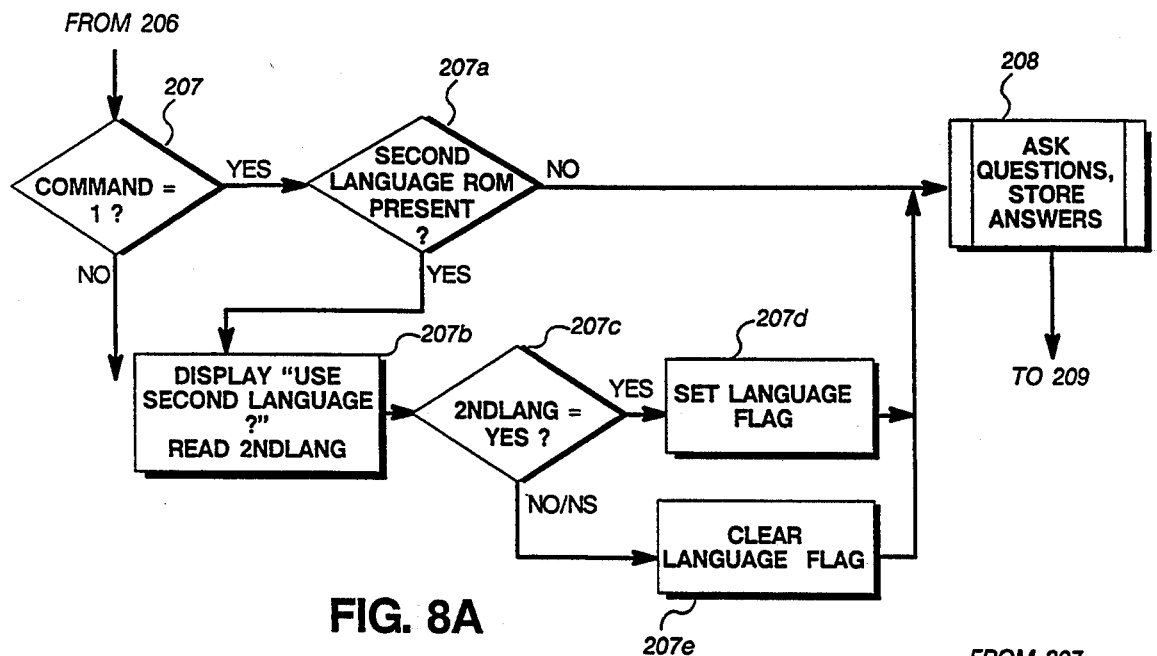
FIGS. 8A, 8B, and 8C are partial flowcharts showing how portions of the program of FIG. 7 can be modified to give the option of a second language for the display and printed reports of the test selector.

If the second language ROM 2 of FIG. 5 is present, there must be additional steps added to the Main Menu routine to allow the option of using the second language. For example, the partial flowchart of FIG. 8A adds such steps in FIG. 7 between steps 207 and 208. If in FIG. 7 command integer 1 is selected, Step 207 of FIG. 8A is "YES" transferring control to Step 207a which checks to see if an additional language ROM 2 is present. If it isn't, Step 207a is a "NO" and the normal path to the subroutine of Step 208 is followed.

But if the second language ROM 2 is present, a "YES" at Step 207a causes Step 207b to put "USE SECOND LANGUAGE?" on display 22 The staffer's response is either "YES" "NO" or "NOT SURE" read from the Patient Keypad, which is stored as 2NDLANG. If 2NDLANG is a "YES" at Step 207c, a LANGUAGE flag is set at Step 207d, and the program moves on to subroutine 208. Subroutine 208 can then check to see if the LANGUAGE flag is set, and if it is, get text for display 22 from locations in ROM 2 rather than in ROM1, causing the second language to be displayed to the patient.

Even if the second language ROM 2 is present, the staffer may have decided to use the primary language, in which case 2NDLANG will be a "NO" or NOT SURE at Step 207c, and the LANGUAGE flag will be cleared at Step 207e before a branch to subroutine 208.

Figure 8B:
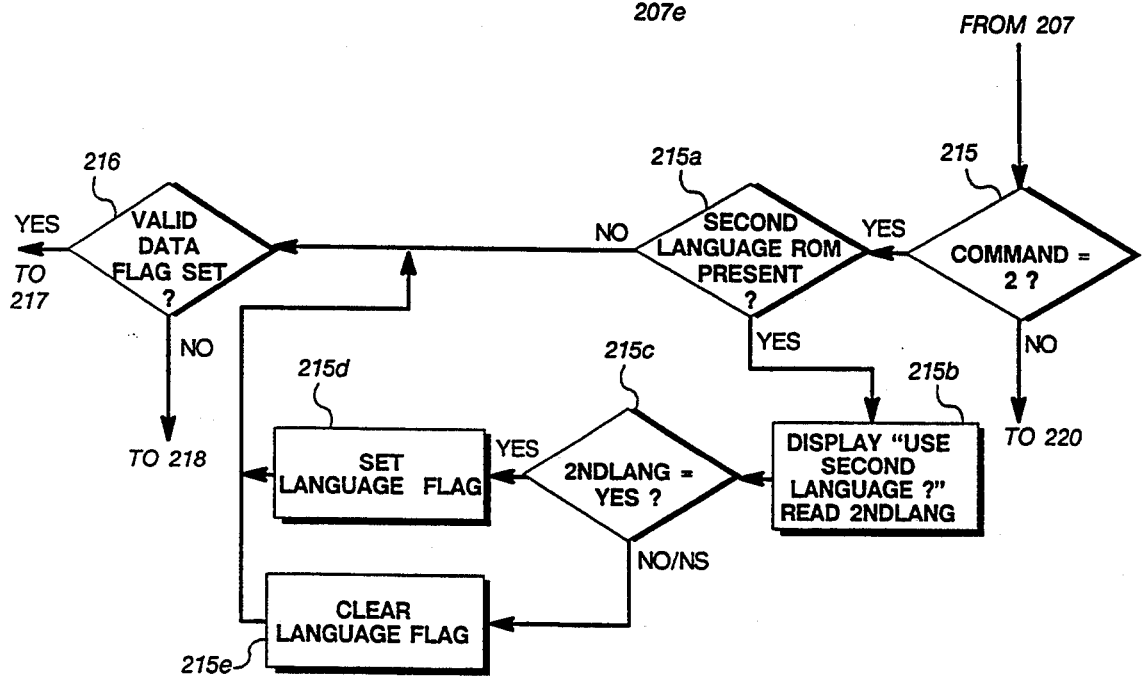
Figure 8C:
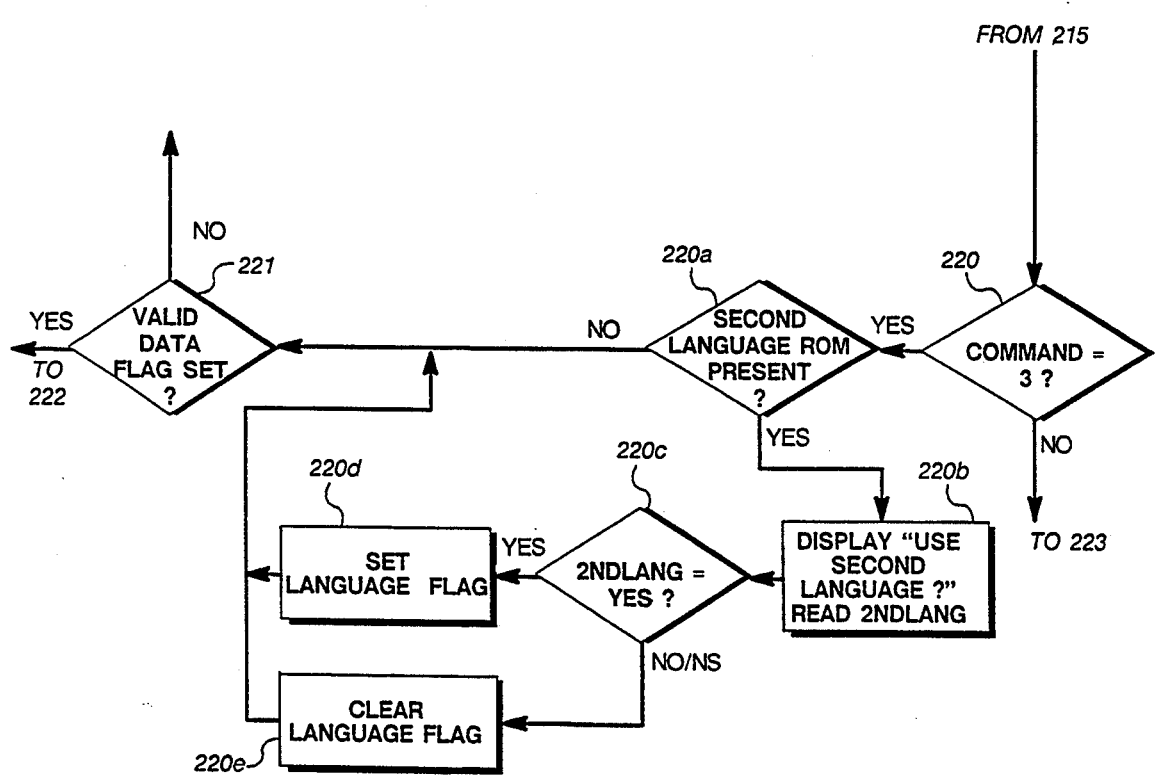

In a similar manner, as shown in FIG. 8B, second language steps can be inserted between Steps 215 and 216 of FIG. 7 to affect the language in which the Doctor's Report is printed. If Step 215a finds that ROM 2 is not present, the usual transfer to Step 216 to check the VALIDDATA flag is made. But if ROM 2 is present Step 215b puts the question "USE SECOND LANGUAGE?" on the display. If the staffer enters "YES" on the patient keyboard, this is detected by STEP 215c, and the LANGUAGE flag is set at Step 215d. Subroutine 217 of FIG. 7 can check to see if the LANGUAGE flag is set, and if it is, get text for printing from locations in ROM 2 rather than in ROM 1, causing the second language to be used for the Doctor's Report If the staffer instead enters "NO" or "NOT SURE" Step 215e clears the LANGUAGE flag and jumps to Step 216.

The additional steps of FIG. 368C work in a manner similar to those of FIG. 8B, except that they are inserted between Steps 220 and 221 of FIG. 7 and it is the PRINT Q&A Responses subroutine 222 that must use the 2d language text in ROM 2 if the LANGUAGE is set.

d. Ask Questions and Store Answers

Figure 9:
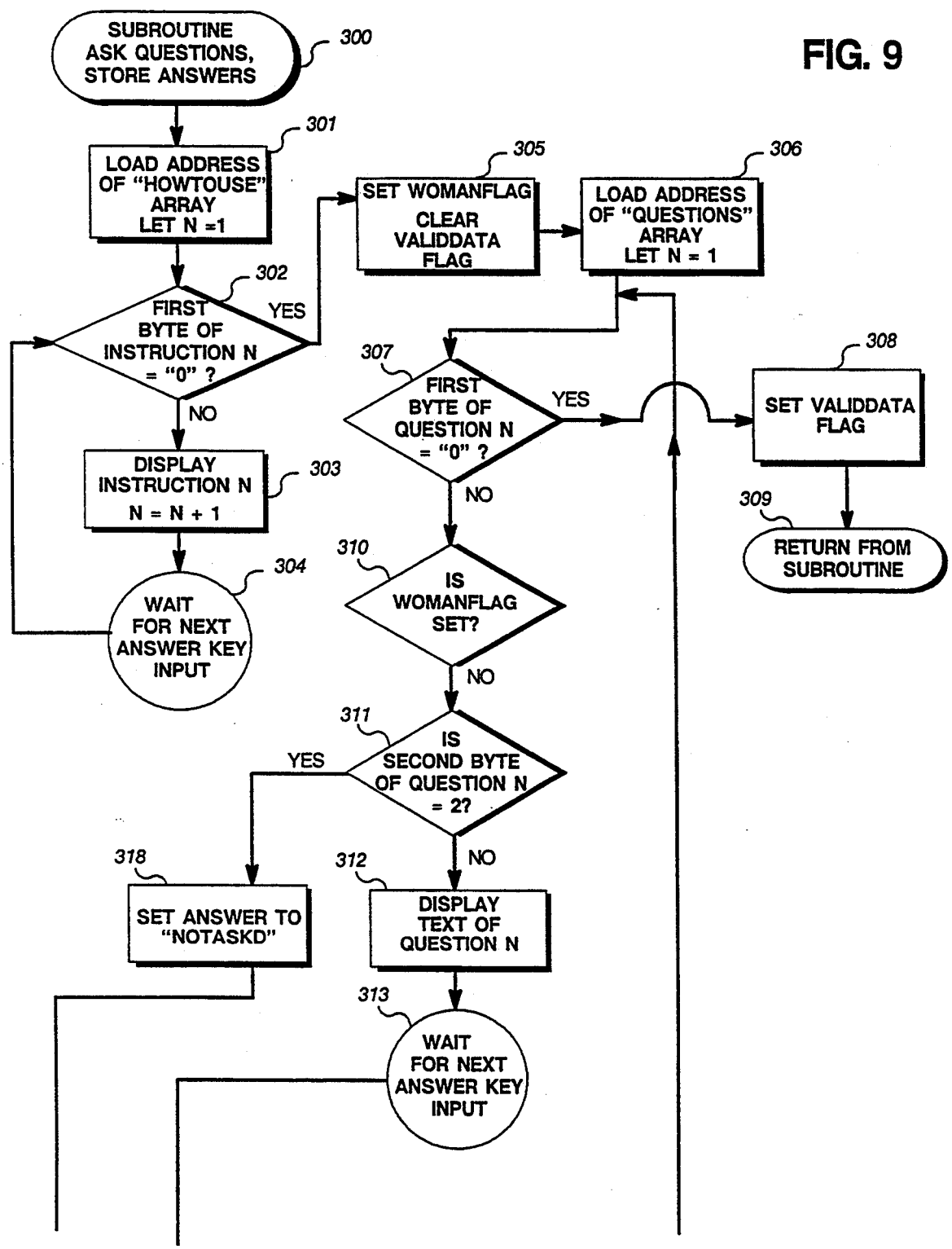
FIG. 9 is a flowchart of a first embodiment of the "Ask Questions, store Answers" subroutine of FIG. 7.
Figure 9:
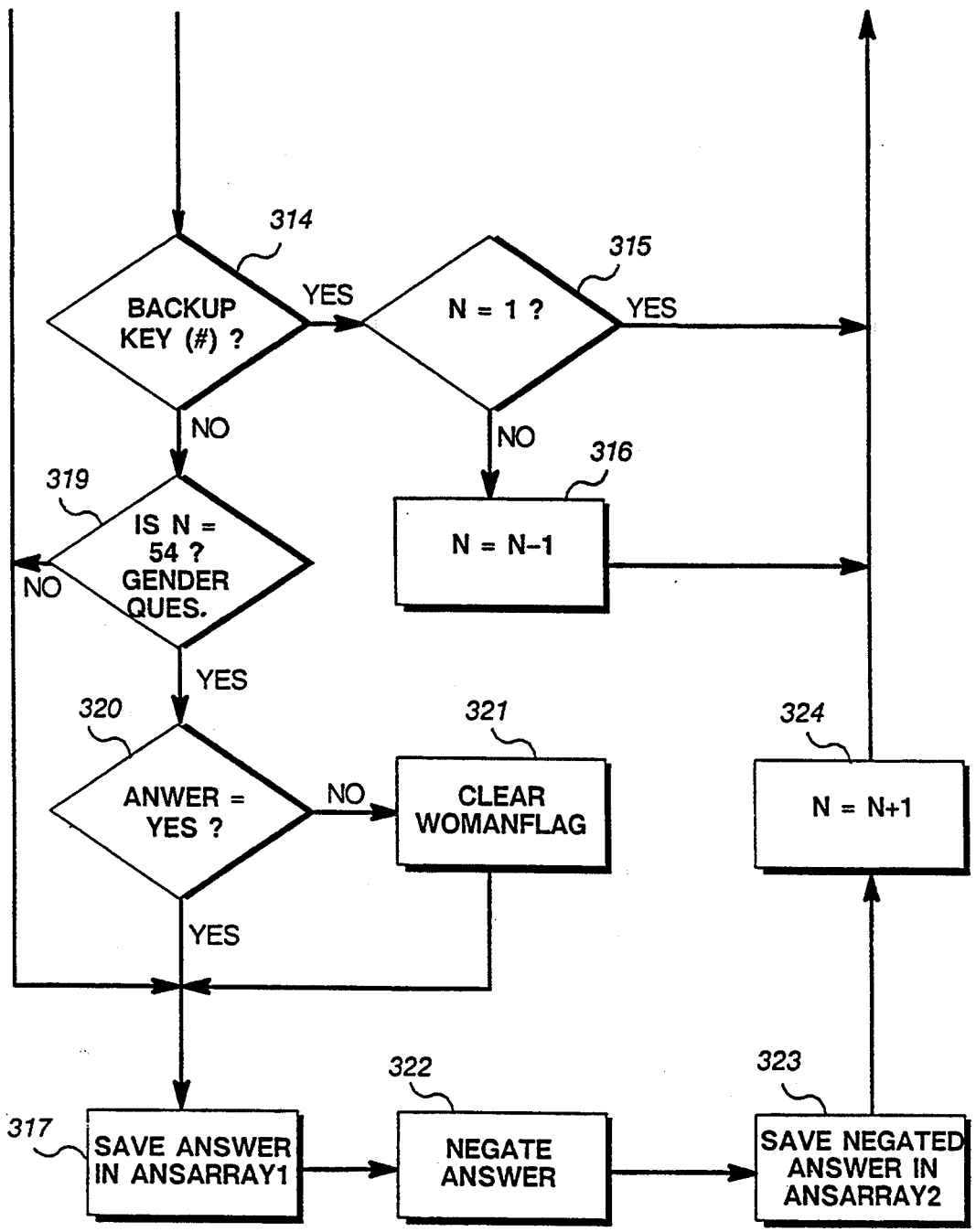

Next, FIG. 9 shows in some detail how the ASK QUESTIONS, STORE ANSWERS subroutine 208 of FIG. 7 is effected. Beginning at Step 300, the address of the array "HOWTOUSE" is loaded and saved for reference. This array has the instruction screens for the patient explaining how the test selector keys are used to answer questions. The data for the instruction screens are saved as character strings in memory, each starting at a known location. The last screen is a dummy which only contains one byte of data, hexadecimal 0 (Oh).

Thus, Step 302 tests the first byte of Instruction N for Oh. The Instruction screens have some other hexadecimal number in the first byte, so Step 303 causes Instruction screen N to be displayed and N incremented. Then Step 304 causes a pause until the next answer keypad input, after which there is a jump to Step 302 to begin to check the first byte the next Instruction Screen.

Finally, the first byte in the last (dummy) screen is detected, indicating that all the Instruction Screens have appeared to the patient on display 22. A jump is made to Step 305 where the sex or WOMANFLAG is set as a default and the VALIDDATA flag cleared as a default.

The address of the QUESTIONS array is found and stored at Step 306, and the index N is restarted at N=1.

Before proceeding further, it is necessary to explain the format and contents related to each question stored in the read only memory ROM 1. Each question for the patient is stored in memory as part of a Question Structure of the form:

<Question Number> <Assoc Flag> <Question Class> <Text String>

This formatting can be understood as follows:

<Question Number> is the number of the question, except in the case of the last or dummy question, which is given a Question Number of Oh to indicate the end of the questions.

<Assoc Flag> is a code in which "0" indicates a default or ordinary question. A "1" indicates that the question has an associated text string, such as a follow-up question or a comment. A "2" indicates a question that should only be asked of females.

<Question Class> is a sorting code for identifying the type of question, as follows: 1=Lab Test Question, 2=Anesthesia Question, 3=General Heath Question.

<Text String> is a string of ASCII characters making up the text of the question, including any characters reserved to represent carriage returns and line feeds, with the last byte being a Oh to indicate that the string has ended.

If <Assoc Flag> is 1, the Question Structure further includes from one to three more character strings, identified as:

<Follow-up Question String>
<YES Comment String>
<NO Comment String>

The follow-up question is necessary when the patient indicates some complication. For example, if the patient says he or she had an EKG test in the last two months, the follow-up asks where, providing a blank line to be filled in the printout of Questions and Answers.

The YES or NO comment strings put short statements in the report to the doctor of points to be noticed because of a YES or NO reply. For example, "Patient has loose teeth". "Patient may not have had an EKG in the last 2 months."

Returning to the ASK QUESTION, STORE ANSWERS subroutine of FIG. 9, at Step 307 the first byte of the Nth Question Structure in the Array is examined to see if it is 0. If it is, we must have reached the dummy question that indicates the end of the questions. A branch is made to Step 308, which sets the VALID-DATA flag and at Step 309 a Return From Subroutine is made.

However, at first N=1 and the answer at Step 307 is "NO". Although Step 310 checks to see if the WOMANFLAG is set, which initially it always is because of Step 305. Later, Question 54 will ask if the patient is a woman, clearing the WOMANFLAG if the patient answers that he is a man. Questions that follow Question 54 can then be omitted, depending on the patient's sex.

Therefore, at first the program will always jump to Step 312, which puts the text of the Nth question on the display and waits for an answer at the patient's keyboard. Assuming there is no backup to an earlier question, and the gender question (N=54) has not been reached, Step 317 saves the patient's YES, NO, or NOT SURE answer as distinguishable binary codes in the Nth entry of an answer array ANSARRAY1. At Step 322 the two's complement of the answer code is saved in a second answer array ANSARRAY2, N is incremented by Step 324 and a jump is made back to Step 307.

The reason for having a second answer array that is the negative (two's complement) of the first array is for checking against loss or corruption of data. The codes in ANSARRAY1 can be added to yield some number D. The codes in ANSARRAY2 can be added to yield some number $D_*$, which should be the complement of D. Therefore, only if the data is not corrupted $D+D^*=0$. That is, array ANSARRAY2 enables a simple integrity check of the data before using or printing the stored data.

Now suppose the gender question 54 "ARE YOU A FEMALE?" is reached at Step 319. The answer at both Steps 319 and 320 will be "YES" for a female, leaving the WOMANFLAG set. A male will answer "NO" at Step 320, causing Step 321 to clear the WOMANFLAG.

With the patient's sex determinable by WOMANFLAG, Step 310 becomes meaningful. As previously explained, if the second byte of a Question Structure is 2h, the question is only to be asked of females Therefore, suppose Step 310 determines that "NO" the WOMANFLAG is not set (patient is a male), and Step 311 determines that the question's second byte indicates that it is for women only. A branch is made to Step 318, which sets the answer to "NOTASKD" (not asked). By contrast, if Step 312 does not find a 2 in the second byte of a Question Structure, the question is displayed to both males and females by Step 312.

We turn next to the backup steps 314, 315, and 316 in FIG. 9. Step 314 determines if the key pressed was the backup key on the control pad. If it was, Step 315 checks to determine if the current value of N is 1, the lowest it can be. If it is, N is not decremented, i.e. there is no backup because we are already at Question 1. But if N is greater than 1, it is decremented by Step 316, which backs up the display to the previous question. Logic for the backup mode to skip over questions that were not asked due to gender, is also built in.

As explained above, the ASK QUESTIONS, STORE ANSWERS routine ends when at Step 307 a question is encountered whose question number is 0. A branch is then made to Step 308 to set the VALID-DATA flag, after which Step 309 executes a Return From Subroutine.

e. Printing A Doctor's Report

Once a set of valid answers has been taken from the patient, from the main menu (FIG. 3B) the medical staffer can choose to print a report for the doctor, including suggested tests. The staffer takes back test selector 20 from the patient, and using printer port 21e of FIG. 1, connects it to a standard serial printer 42 as shown in FIG. 2.

To print the report for the doctor, at the main menu (FIG. 3B, FIG. 7, Step 206) the staffer selects command 2. Because Step 207 is "NO" and Step 215 is "YES" next Step 216 checks to see if the VALIDDATA flag is set. If it is, there is a valid set of data to print, and subroutine PRINT DOCREPORT is called at Step 217.

Figure 10:
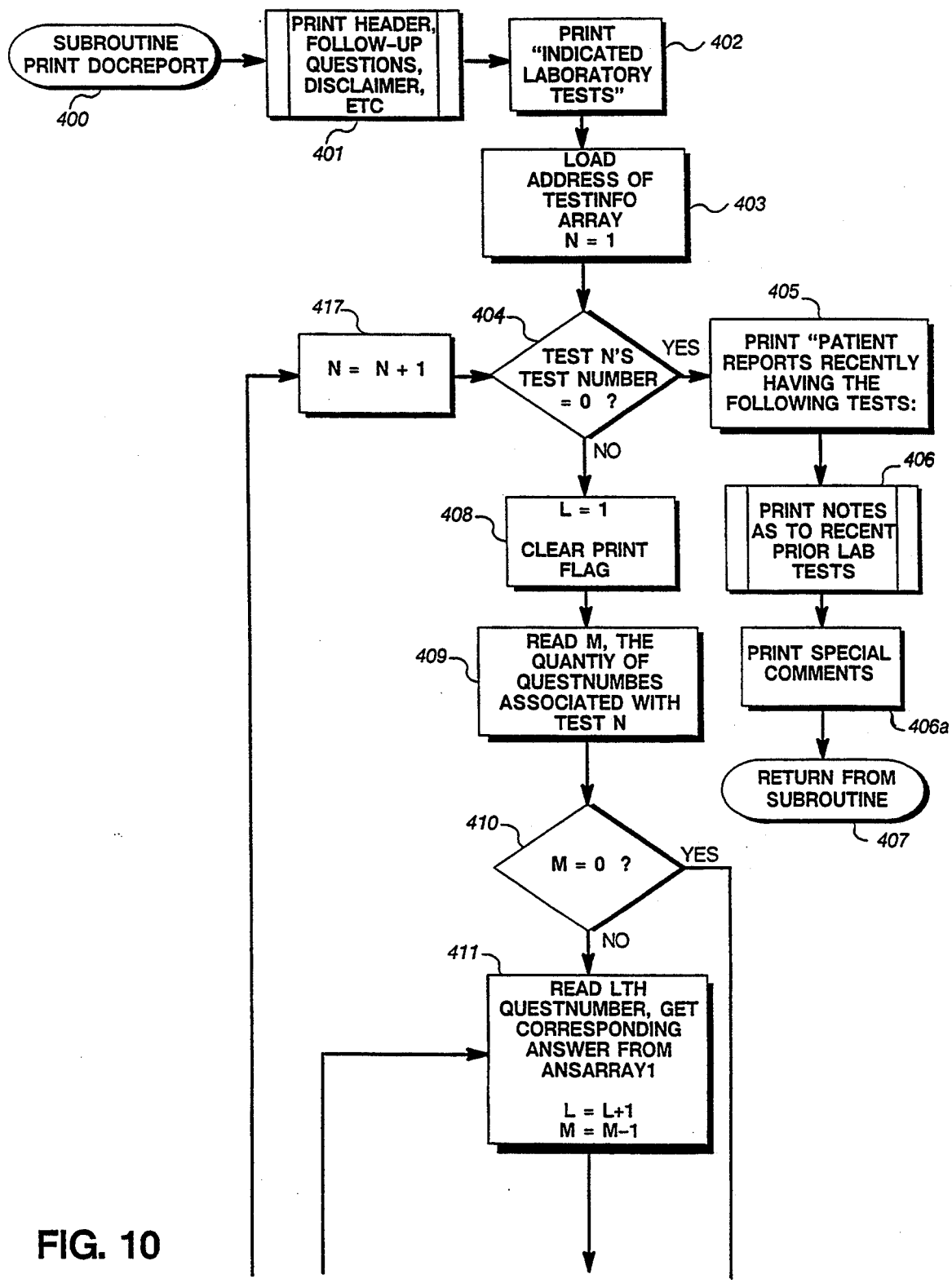
FIG. 10 is a flowchart of the "Print Docreport" subroutine of FIG. 7, which prints a report for a doctor.
Figure 10:
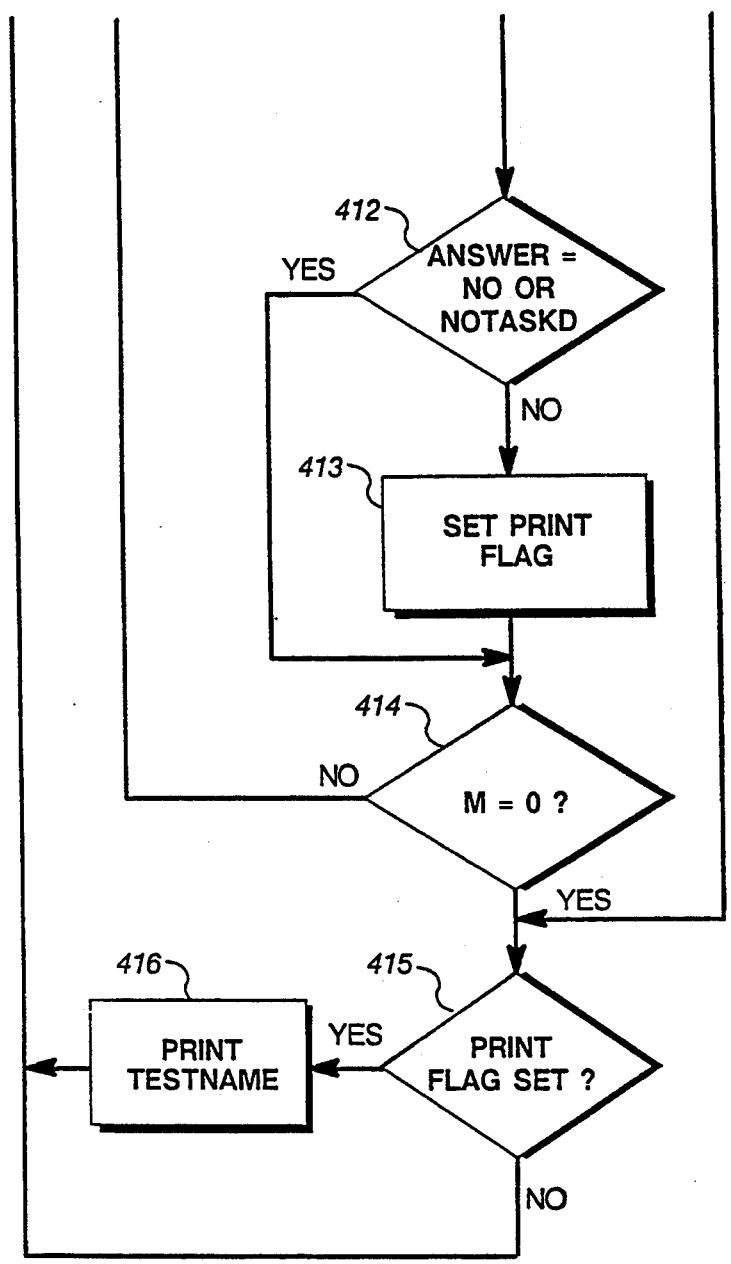

The PRINT DOCREPORT subroutine is shown in more detail in FIG. 10. The subroutine begins at Step 400 and moves to Step 401, where a header for the report is printed (see Appendix I) that includes blanks for handwritten insertion of patient information.

Next, any Follow-Up Questions associated with questions to which the patient has answered YES are printed. For example, if the patient has answered "YES" he or she has allergies, the follow-up question printed will be:

WHAT ARE YOU ALLERGIC TO?_

The text of a Follow-Up Question is stored in memory in the previously mentioned Question Structure after the question to which it is associated. Also stored in memory is an array called SPCQST which tells STEP 401 which YES/NO questions have associated Follow-Up Questions, which answers (YES, NO, NOT SURE) should cause a Follow-Up Question to be printed, and the address of each Follow-Up Question.

Next, Step 401 prints a disclaimer (see Appendix I) that includes information as to the basis for the test recommendations and a cutoff date beyond which the test guidelines stored in the ROM memory should not be regarded as valid because they may need updating.

Step 402 then prints a heading "INDICATED LABORATORY TESTS". Then at Step 403 an indexing number N is set equal to 1, and the address of an array TESTINFO, which stores information about each test, is loaded.

For each test, there is an information entry in TESTINFO according to the following format:
  <TESTNO> The number of the test.
  <QUESCOUNT> A number indicating how many Question Numbers are stored in <QUESADDS>
  <QUESADDS> A series of address pointers, each indicating the address of a question that might give rise to an order for this test.
  <TESTNAME> The name of the test (ASCII string).

The last test entered in TESTINFO is a dummy, the TESTNO of which is 0 to indicate there are no more tests.

Therefore, at Step 404 the TESTNO of the Nth item in TESTINFO is checked to see if it is zero. If it is, the program has reached the final or dummy test and can proceed to Step 405. However, usually the TESTNO of the Nth item in TESTINFO is not zero, and the program proceeds to Step 408, where an indexing variable L is set to 1 and a flag called PRINT is cleared.

Then at Step 409 the variable M is set equal to the QUESCOUNT associated with the Nth item in TES- TINFO. If M=QUESCOUNT=0, there is no question that could give rise to an order for the Nth test, and a jump is made to Step 415. Since the PRINT flag was cleared in Step 408, the result at Step 415 will be a "NO" causing a jump to Step 417, which increments indexing variable N.

However, usually M=QUESCOUNT>0 because one or more questions could give rise to an order for the Nth test. At Step 411 the Lth question address pointer stored in the field <QUESADDS> is read, and the patient's corresponding answer for this question pointed to is read from the array ANSARRAY1.

For example, suppose N=1, so that the printing program is computing whether to set the PRINT flag to print the name of the 1st TEST under the heading "INDICATED LABORATORY TESTS". Step 409 goes to item 1 of the array TESTINFO, where it finds the entries:

| | |
|---|---|
| <TESTNO> | 1 |
| <QUESCOUNT> | 13 |
| <QUESADDS> | Q01, Q02, Q03, Q04, Q05, Q06, Q07, Q08, Q10, Q11, Q12, Q54, Q65 |
| <TESTNAME> | The name of the test (ASCII string). |

Suppose the current value of L=1. Then the first (L=1) question pointer Q01 is read from the field QUESADDS, and used to access the information about the indicated question in the QUESTIONS array. In particular, the indicated Question Number is found to be "1" which allows the corresponding answer to be read from ANSARRAY1.

If at Step 412, the answer is found not to be "NO" (i.e. found to be YES or NOT SURE), Step 413 will set the PRINT flag. Later, when the program reaches Step 415, the set PRINT flag will cause the test's name to be printed by Step 416.

If at Step 412 the answer is "NO" there is a jump to Step 414 so the PRINT flag will not be set. Step 414 checks to see if M=0, which would indicate that there are no more question address pointers to be read from field QUESADDS. If M≠0, there is a jump to Step 411 where the index variable L is incremented and the index variable M is decremented.

Thus, any of the question numbers associated with a test can, for a YES or NOT SURE answer, cause the PRINT flag to be set at Step 413. When Step 414 finds that M=0, the PRINT flag is checked by Step 415, and if it is set, the TESTNAME is printed at Step 416. Then the program proceeds to Step 417 where the indexing integer N is incremented to proceed to the next test.

If none of the answers to the questions associated with the Nth Test has set the PRINT flag, at Step 415 the answer is "NO", and there is a jump to Step 417 where N is incremented to the next test in TESTINFO.

As mentioned above, as N is incremented, eventually the final or dummy test whose TESTNUMBER is "0" is reached. Then the result of Step 404 is a YES, and Step 405 prints a heading "PATIENT REPORTS RECENTLY HAVING THE FOLLOWING TESTS:". To determine what comments should be printed about past tests, reference is then made to the array STATEMENTS. This array gives pointers to any YES Comment String, NO Comment String, or NOT SURE Comment String which follows a Lab Test Question.

The patient's stored answers determine which of these three comment strings is printed.

For example, question 67 asks if the patient has had a blood test in the last six months. The YES Comment String to be printed at Step 406 is "PATIENT HAS HAD A BLOOD TEST IN THE LAST 6 MONTHS.", and the NO and NOT SURE Comment Strings are "PATIENT MAY NOT HAVE HAD A BLOOD TEST IN THE LAST 6 MONTHS."

After these lab test comments are printed at the end of the doctor's report, Step 406A prints Comment Strings about the patient that will be helpful to the doctor's selection of tests. For example, if the patient answered "YES" that he or she wears dentures, a YES Comment String "PATIENT WEARS DENTURES" will be printed. A table of which questions have a printable associated YES Comment String or NO Comment String is stored in an array STATEMENTS.

After these special comments are printed, Step 407 executes a Return From Subroutine.

f. Printing Questions & Answers

If a set of valid answers has been taken from the patient, from the main menu (FIG. 3B) the medical staffer can also choose to print out the questions together with the patient's answers, including follow-up questions with blanks for handwritten answers. As in the case of the Doctor's Report, test selector 20 is connected to a standard serial printer 42 as shown in FIG. 2 via printer port 21e.

To print the questions and answers, at the main menu (FIG. 3B, FIG. 7, Step 206) the staffer selects command 3. Because Steps 207 and 215 are "NO" and Step 220 is "YES" next Step 221 checks to see if the VALIDDATA flag is set. If it is, there is a valid set of data to print, and the subroutine PRINT Q&A RESPONSES is called at Step 222.

Figure 11:
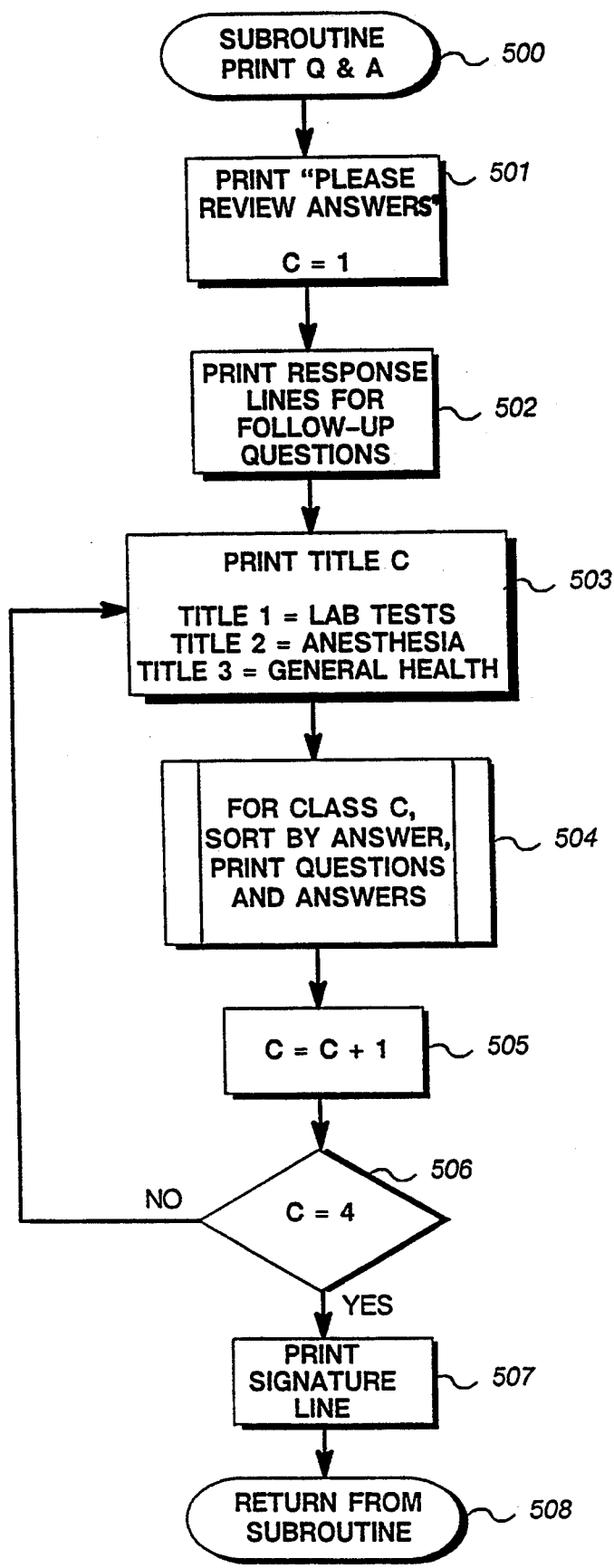
FIG. 11 is a flowchart of the "PrintQ&A" subroutine of FIG. 7, which prints a list of questions presented and the patient's answers, sorted by answer and question type.

The PRINT Q&A RESPONSES subroutine is shown in more detail in FIG. 11. The subroutine begins at Step 500 and moves to Step 501, where a header for the report is printed (see Appendix II). A line is printed that instructs the patient, "PLEASE REVIEW YOUR ANSWERS". An indexing variable C is set equal to 1.

Next, any Follow-Up Questions associated with questions to which the patient has answered YES are printed with blanks to be completed by the patient. This is done in a manner similar to that described for Step 401 of the subroutine PRINT DOCREPORT of FIG. 10. The Follow-Up Question is stored in memory in the Question Structure after the question to which it is associated. The array called SPCQST tells STEP 502 which YES/NO questions have associated Follow-Up Questions, which answers (YES, NO, NOT SURE) should cause a Follow-Up Question to be printed, and the address of each Follow-Up Question.

The questions are divided into groups separated by titles printed at Step 503. The title printed at Step 503 depends on the current value of the variable C: 1=LAB TESTS, 2=ANESTHESIA, 3=GENERAL HEALTH. For each value of C (1, 2, 3), Step 504 calls the subroutine SORT AND PRINT QUESTIONS AND ANSWERS of FIG. 12 to print the questions and answers having the Question Class which corresponds to the current title. Within a title, the order of printing is questions answered "YES" questions answered "NOT SURE" and questions answered "NO". For example, when C=1, calling the subroutine of FIG. 12 will only cause the questions and answers related to LAB TESTS to be sorted out and printed in this order.

Then at Step 505, the variable C is incremented so questions and answers under the next title can be printed. Assuming that there are just three titles, a check is made at Step 506 to see if C=4. If it does not, there is a jump back to Step 503 for the next title. But if C=4 at Step 507, there are no more titles and a signature line for the patient is printed under the words "THE ABOVE ANSWERS ARE CORRECT AS TYPED". After the signature line is printed, there is a Return From Subroutine at Step 508.

Figure 12:
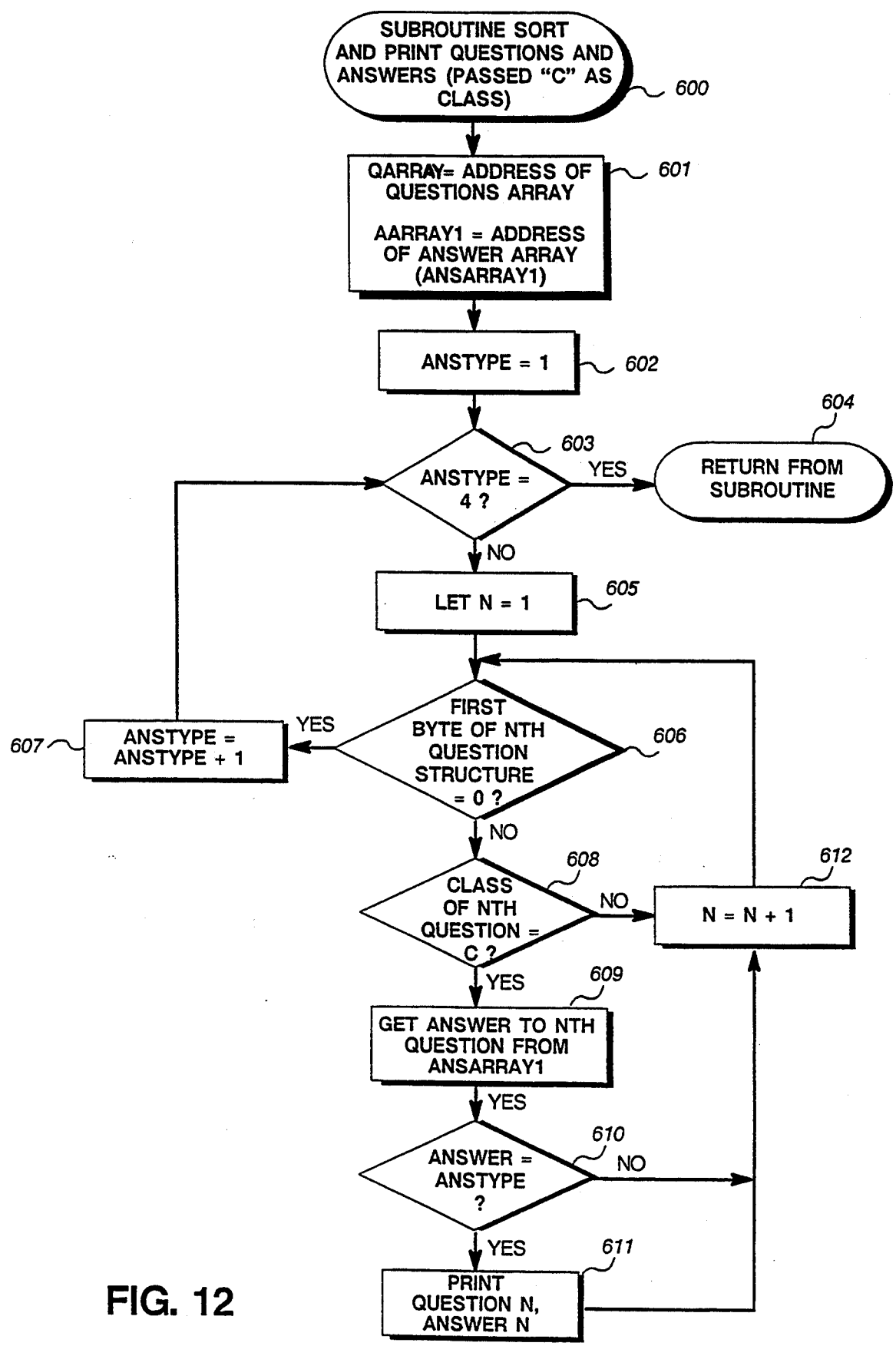
FIG. 12 is a flowchart of the "SORT AND PRINT QUESTIONS AND ANSWERS" subroutine used in the PrintQ&A subroutine of FIG. 11.

The SORT AND PRINT QUESTIONS AND ANSWERS subroutine is shown in more detail in FIG. 12. The routine begins at Step 600 with some given value of C (1, 2, or 3) from the calling subroutine of FIG. 11. At Step 601 the respective addresses of the QUESTIONS ARRAY and first ANSWER ARRAY are noted. At Step 602 an indexing variable ANSTYPE is initially set to 1.

The variable ANSTYPE has the following meanings 1=YES answer, 2=NOT SURE answer, 3=NO answer, 4=NOTASKD (end of printed answers). Therefore, at Step 603 a check is made to see if the indexing variable ANSTYPE equals four. If it does, there is a Return From Subroutine at Step 604.

However, initially ANSTYPE is one because of Step 602, and the program proceeds to Step 605 where an indexing integer N is set to 1. Then at Step 606, the first byte of the Nth Question Structure stored in the questions array QARRAY is read. If it equals zero, the dummy Question Structure has been reached that indicates there are no more questions to process.

However, usually the first byte is not zero, in which case Step 608 compares the Question Class of the Nth Question Structure with the value of C input to the subroutine. If the Question Class does not match C, a jump is made to Step 612, where N is incremented and a jump made back to Step 606 to check the first byte of the next Question Structure.

When the Question Class of the Nth Question Structure matches the value of C at Step 608, the corresponding answer is obtained from answer array ANSARRAY1 by Step 609. If the answer matches the current value of ANSTYPE, the Question and its corresponding Answer are printed at Step 611. Otherwise, the Question and Answer are skipped by jumping to Step 612, where the variable N is incremented. Then there is a return to Step 606 to read the first byte of the next question structure.

For each value of ANSTYPE, eventually N is incremented at Step 612 until the dummy Question Structure is reached, causing a "YES" at Step 606. Then Step 607 increments ANSTYPE to the next type of answer. Eventually, Step 607 causes ANSTYPE to equal four, which is detected by Step 603 to cause a Return From Subroutine at Step 604 as mentioned above.

Thus, for a given category of question C, the subroutine of FIG. 12 first prints all the questions answered "YES" then all those answered "NOT SURE", and then all those answered "NO". Within a category, the answer given to a question determines its order in the printout.

In the first embodiment of the invention so far described, the subroutine ASK QUESTIONS, STORE ANSWERS of FIG. 9 processes each question in sequence (FIG. 13C), but if the WOMANFLAG is CLEAR certain questions only for females are not displayed (FIG. 9, Step 311) and automatically answered "NOTASKD" (not asked) by Step 318. As shown in FIG. 13A, the flag check FCh causes question $Q_i$ to be skipped when the WOMANFLAG is CLEAR and instead processing proceeds to question $Q_{i+1}$.

For a male patient, if the program has to be backed up from question $Q_{i+1}$, logic is built in so that backup key 37 skips question $Q_i$ and returns to previous question $Q_{i-1}$, here assumed to be a general question for both men and women. Thus, this simple automatic skipping of certain questions irrelevant to the particular patient does not greatly complicate use of backup key 37.

In the subroutine PRINT DOCREPORT, which prints a report to the doctor, questions whose answer is "NO" or "NOTASKD" do not cause the associated test to be printed (Step 412). The subroutine SORT AND PRINT QUESTIONS AND ANSWERS of FIG. 12 treats questions having the answer "NOTASKD" as a forth type whose printing is skipped by the action of Step 603.

A second embodiment of the invention allows for more general branching to further questions in accordance with the patient's answers and provides a means for storing the return path needed to support backup key 37. A source code listing of the control program for the second embodiment is attached as Appendix IV.

As shown in FIG. 13D, in the second embodiment the next step of the control program after displaying question $Q_i$ depends on whether the answer to question $Q_i$ is YES (Y) or NO (N). In the general case, as shown in FIG. 13B, we must also allow for the alternative paths to converge at certain questions, such as $Q_{13}$ and $Q_{18}$. To move backwards to previous questions along the correct alternative paths requires special support for backup key 37.

As shown even more generally in FIG. 13E, each question $Q_i$ can be followed by a branch to one of three different paths Y, N, NS, corresponding to YES, NO, and NOT SURE. FIG. 13F shows the tree-like structure of the possible paths of the program when the next question to be asked depends on whether the answer is YES, NO, or NOT SURE.

To enable such branching, the previously mentioned Question Structure stored for each question in the QUESTIONS array is augmented as follows:

<Question Number> <Assoc Flag> <Question Class>
<Text String>
<Branchflag> <Next/Yes Question Pointer>
[<No Question Pointer>]

The additional parts of the Question Structure which enable branching are a BRANCHFLAG, a NEXT/YES QUESTION POINTER and a NO QUESTION POINTER. If a particular question does not need branching, such as question $Q_i$ of FIG. 13C, the BRANCHFLAG is CLEAR, the NEXT/YES QUESTION POINTER is used as a pointer to the next question $Q_{i+1}$, and the NO QUESTION POINTER is not present.

A question leading to a YES or NO alternative (see FIG. 13D) has its BRANCHFLAG SET. The NEXT/YES QUESTION POINTER points to the next question that should follow a "YES" and the No Pointer points to the next question that should follow a "NO". For purposes of branching, the test selector can be designed to always treat an answer of "NOT SURE" as either a "YES" or a "NO". Alternatively, the test selector's Question Structure can be further augmented to add a separate pointer [<Not Sure>] for a third alternative as shown in FIG. 13E.

Figure 14:
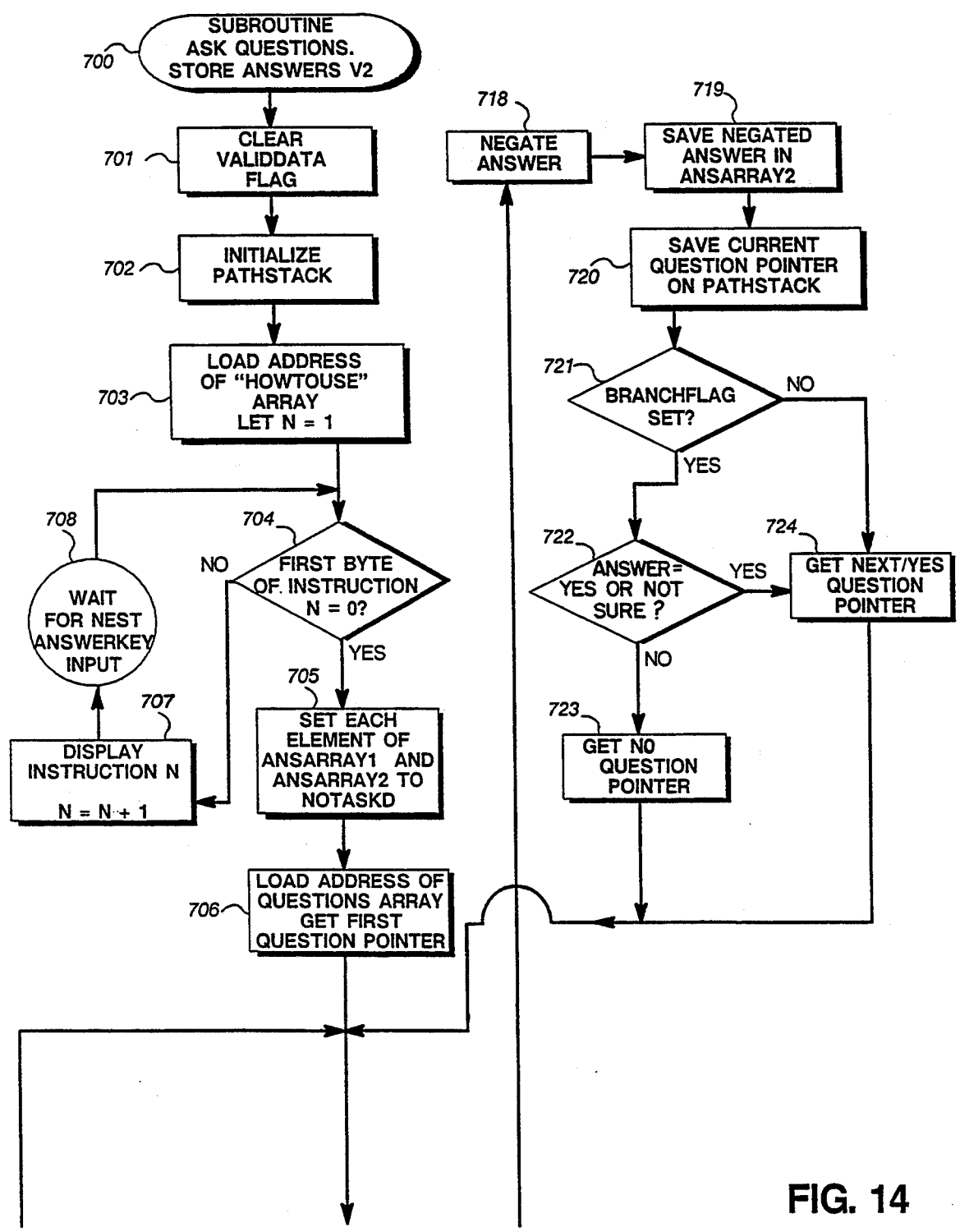
FIG. 14 is a flowchart of a second embodiment of the "Ask Questions, Store Answers" subroutine of FIG. 7.
Figure 14:
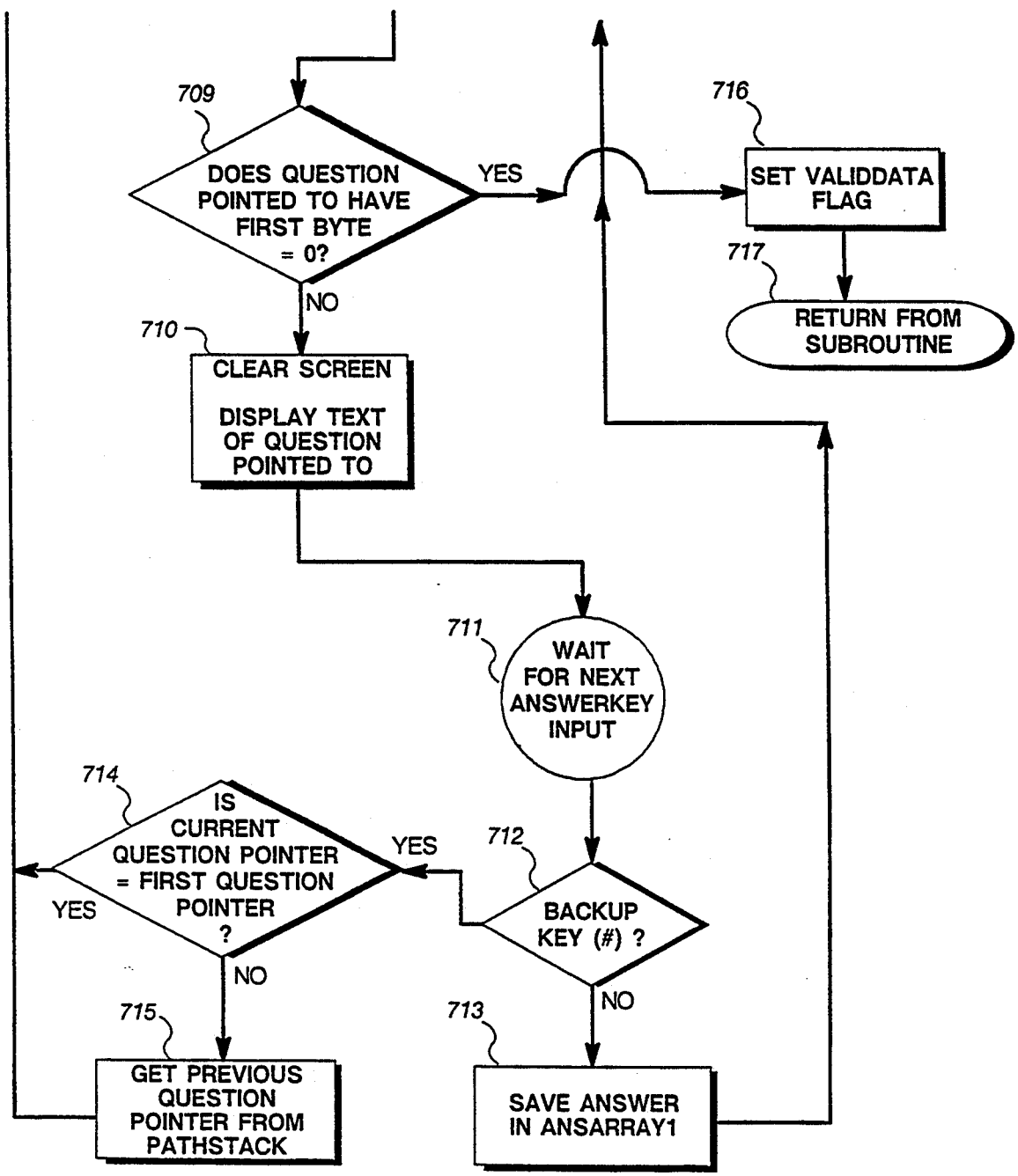

For example, to enable branching which treats an answer of "NOT SURE" like a "YES" FIG. 14 shows a subroutine ASK QUESTIONS, STORE ANSWERS V2 to be substituted for the first embodiment's ASK QUESTIONS, STORE ANSWERS subroutine of FIG. 9. Beginning at Step 700, the VALIDDATA flag is cleared at Step 701 and a portion of RAM memory 142 (FIG. 5) is initialized as a first-in-last-out stack called PATHSTACK for question address pointers. Then the address of the array "HOWTOUSE" is loaded at Step 703, and an index integer N set initially to 1.

Step 704 tests the first byte of Instruction N for 0h. Since the Instruction screens have some other hexadecimal number in the first byte, a jump is made to Step 707, which causes Instruction screen N to be displayed and N incremented. Then Step 708 causes a pause until the next answer keypad input, after which there is a jump to Step 704 to check the first byte of the next Instruction Screen. Finally, a first byte of 0h in the last (dummy) screen is detected, indicating that all the Instruction Screens have appeared to the patient on display 22. The program proceeds to Step 705 where each element of the two answer arrays ANSARRAY1 and ANSARRAY2 is initialized to "NOTASKD" (not asked).

The address of the QUESTIONS array is loaded at Step 706, and the first question pointer used to obtain the address of the Question Structure for the first question. The first byte of this Question Structure is examined at Step 709 to see if it is 0. Usually it is not, so the program proceeds to Step 710 which clears the screen and displays the text of the question pointed to. Then Step 711 waits for an answer to be input at the patient's keyboard.

Assuming at Step 712 that the backup key # has not been pressed, Step 713 saves the patient's YES, NO, or NOT SURE answer as distinguishable binary codes in an corresponding entry of an answer array ANSARRAY1. Then Step 718 determines the two's complement of the answer code, and Step 719 saves this in a second answer array, ANSARRAY2.

If instead Step 712 finds that the backup key on the control pad was pressed, Step 714 determines if the current question pointer is that pointing to the first question. If it is, there is no backup because we are already at Question 1. But if Step 714 determines that the question currently pointed to is greater than 1, Step 715 pops the pointer for the previously asked question off the PATHSTACK. Then a jump is made back to Step 709 to process the previously asked question.

After Step 719 has saved the two's complement of an answer in ANSARRAY2, Step 720 pushes the current question pointer onto the PATHSTACK. If Step 721 finds that the BRANCHFLAG is SET, Step 722 determines if the patient's answer is NO. If it is, Step 723 uses the NO QUESTION POINTER of the current question for the address of the next question to be asked, and a branch is made back to Step 709.

If instead the patient's answer is "YES" or "NOT SURE" Step 724 uses the NEXT/YES QUESTION POINTER of the current question for the address of the next question, followed by a branch back to Step 709.

If Step 721 finds that the BRANCHFLAG is CLEAR, the answer to the current question does not cause branching into alternate paths. Step 724 uses the NEXT/YES QUESTION POINTER of the current question for the address of the next question to be asked, and there is a branch back to Step 709.

The ASK QUESTIONS, STORE ANSWERS V2 routine ends when at Step 709 a question is encountered whose question number is 0. A branch is then made to Step 716 to set the VALIDDATA flag, after which Step 717 executes a Return From Subroutine.

In this manner, the PATHSTACK, BRANCHFLAG, NEXT/YES QUESTION POINTER, and NO QUESTION POINTER of the second embodiment enable more general branching to further questions in accordance with the patient's answers, without sacrificing the function of backup key 37. This enables the questions asked to be highly relevant and detailed with respect to the patient's age, sex, history and condition, and facilitates the asking of follow-up questions. Since the answer arrays are initialized to "NOTASKED" it is easy for the subroutines DOCREPORT and PRINT-Q&A to ignore unasked questions.

The invention provides a compact, portable automatic test selector for taking patient histories which is easily used, even by bed-ridden patients, and especially adapted for the selection of medical and pre-operative tests. The test selector is easily connected to a printer to print out a report to the doctor of recommended medical and/or preoperative tests and a sorted list of the questions and the patient's answers. It can also be attached to a suitable computerized work station. In addition, there is provision for the patient to review and supplement the answers.

While the principles of the invention have been described above in connection with specification apparatus and applications, it is to be understood that this description is intended only by way of example and not as a limitation on the scope of the invention. Therefore, the following claims are to be construed to cover all equivalent structures.

The invention claimed is:

1. In a data-processing display device of the type including a hand-holdable, battery-operated digital computer having display means, patient input means, a programmable central processor, non-volatile means for storing a program for said processor, means for storing operating data, and means for storing temporary data, the improvement wherein:
said operating data storage means includes one or more predetermined questions directed to the medical history of a patient;
said display means and said input means are the exclusive means by which said patient may interact with said device; and
said hand-holdable, battery-operated digital computer comprises supervisor input means separate from said patient input means for receiving supervisory commands, means for selectably rendering said supervisor input means unrecognizable as an input means; and means operable by a supervisor for selectably making said supervisor input means recognizable as an input means.

2. The improvement of claim 1 wherein said supervisor input means is responsive to at least one supervisory command to enable a prior one of the series of question to be displayed on the display and to enable a patient who has already operated the patient input means to nevertheless replace the patient's answer stored in the temporary data storage means with a substitute answer selected by the patient.

3. The improvement of claim 1 wherein:
said patient input means comprises a limited number of key means accessible to said patient for selecting and entering answers to said questions; and
each of said key means corresponds to a predefined answer from the set consisting "Yes", "No", "Not Sure", and "Next Question", or their linguistic equivalents.

4. The improvement of claim 1 wherein said supervisor input means is responsive to a predetermined password to inhibit entry of said supervisory commands unless said password has been entered.

5. The improvement of claim 1 wherein said supervisor input means is responsive to a predetermined password to inhibit operation of said patient input means unless said password has been entered.

6. The improvement of claim 1 wherein said means for selectably rendering said supervisor input means unrecognizable as an input means comprises removable means for physically covering said supervisor input means to prevent access thereto.

7. The improvement of claim 1 wherein said means for selectably rendering said supervisor input means unrecognizable as an input means comprises:
a portion of said supervisor input means which is responsive to a predetermined command to reveal a further portion of said supervisor input means.

8. The improvement of claim 1 wherein said patient input means is exclusively responsive to answers or instructions relating to said questions.

9. The improvement of claim 1 wherein:
said device is adapted to operate in a first mode and a second mode, such that:
when said device is operating in said first mode, said supervisor input means is responsive to at least one supervisory command, and said patient input means is disabled; and
when said device is operating in said second mode, said supervisor input means is responsive exclusively to a predetermined password, and said patient input means is responsive to answers to said questions.

10. The improvement of claim 9 wherein said supervisor input means is responsive to said password to cause said device to enter said first mode.

11. The improvement of claim 9 wherein said supervisor input means is responsive to at least one supervisory command to cause said device to return to said second mode.

12. The improvement of claim 1 wherein:
said device is adapted to operate in a first mode and a second mode, such that:
when said device is operating in said first mode, said supervisor input means and said patient input means are both recognizable as an input means to a user; and
when said device is operating in said second mode, said patient input means is recognizable to a suer as an input means, and said supervisor input means is substantially unrecognizable to a user as an input means.

13. The improvement of claim 12 wherein said supervisor input means is responsive to said password to cause said device to enter said first module.

14. The improvement of claim 12 wherein said supervisor input means is responsive to at least one supervisory command to cause said device to return to said second mode.

15. The improvement of claim 1 wherein said patient input means is a first keyboard and said supervisor input mean sis a second keyboard physically spaced from said patient input means.

16. The improvement of claim 1 wherein said patient input means is a first keyboard and said supervisor input means is a second keyboard covered by a removable physical barrier.

17. The improvement of claim 1 wherein said supervisor input means comprises:
a keyboard having a plurality of key means, at least one of which has a visual indicium;
and means for rendering said visual indicium visible or invisible to a user in response to said central processor, whereby said supervisor input means is substantially unrecognizable as an input means when said indicium is invisible.

18. The improvement of claim 17 wherein said processor is responsive to a predetermined command to render said indicium to be visible once again.

19. In a data-processing display device of the type including a hand-holdable, battery-operated digital computer having display means, patient input means, a programmable central processor, non-volatile means for storing a program for said processor, means for storing operating data, and means for storing temporary data, the improvement wherein:
said operating data storage means includes one or more predetermined questions directed to the medical history of a patient;
said display means and said patient input means are the exclusive means by which said patient may interact with said device; and
said hand-holdable, battery-operated digital computer comprises supervisor input means separate from said patient input means for receiving supervisory commands; means for concealing said supervisor input means from said patient; means operable by a supervisor for selectably rendering said supervisor input means visible to said supervisor; and means for rendering said supervisor input means unusable whenever said supervisor input means is concealed.

20. The improvement of claim 19 wherein:
said supervisor input means comprises: a keyboard having a plurality of key means, at least one of which has a visual indicium; and means for rendering said visual indicium visible or invisible to a user in response to said central processor, whereby said supervisor input means is substantially unrecognizable as an input means when said indicium is invisible; and
said device is adapted to operate in a first mode and a second mode, such that:
when said device is operating in said first mode, said supervisor input means is responsive to at least one supervisor command, said indicium is rendered visible, and said patient input means is disabled; and when said device is operating in said second mode, said indicium is rendered invisible, and said patient input means is responsive to inputs including answers to said questions.

21. The improvement of claim 20 wherein said central processor is responsive to a predetermined password to cause said device to enter said first mode.

22. The improvement of claim 20 wherein said central processor means is responsive to at least one supervisory command to cause said device to return to said second mode.

* * * * *